United States Patent
Aubert et al.

(10) Patent No.: US 11,911,636 B2
(45) Date of Patent: Feb. 27, 2024

(54) PROCESS FOR TREATING KERATIN FIBERS USING A PACKAGING ARTICLE COMPRISING AN ENVELOPE AND AN ANHYDROUS COMPOSITION COMPRISING AN OXIDIZING AGENT

(71) Applicant: L'OREAL, Paris (FR)

(72) Inventors: Fabien Aubert, Paris (FR); Frédéric Guerin, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/861,380

(22) Filed: Apr. 29, 2020

(65) Prior Publication Data
US 2021/0046333 A1 Feb. 18, 2021

Related U.S. Application Data

(62) Division of application No. 15/107,319, filed as application No. PCT/EP2014/078855 on Dec. 19, 2014, now abandoned.

(30) Foreign Application Priority Data

Dec. 23, 2013 (FR) ........................... 1363394

(51) Int. Cl.
*A61Q 5/06* (2006.01)
*A61K 8/73* (2006.01)
(Continued)

(52) U.S. Cl.
CPC .............. *A61Q 5/065* (2013.01); *A61K 8/022* (2013.01); *A61K 8/027* (2013.01); *A61K 8/0208* (2013.01);
(Continued)

(58) Field of Classification Search
None
See application file for complete search history.

(56) References Cited

U.S. PATENT DOCUMENTS 3,100,739 A 8/1963 Kaiser et al.
3,376,110 A 4/1968 Shiraeff
(Continued)

FOREIGN PATENT DOCUMENTS

DE 2359399 A1 6/1975
DE 2527638 A1 5/1976
(Continued)

OTHER PUBLICATIONS

Non-Final Office Action for copending U.S. Appl. No. 15/107,319, dated Oct. 31, 2019 (now abandoned).
(Continued)

*Primary Examiner* — Nicole P Babson
(74) *Attorney, Agent, or Firm* — THE MARBURY LAW GROUP, PLLC

(57) ABSTRACT

The present invention relates to a process for treating keratin fibers such as the hair using a packaging article comprising i) an envelope defining at least one cavity, the envelope comprising water-soluble and/or liposoluble fibres, preferably water-soluble fibres; ii) at least one anhydrous oxidizing composition, preferably in paste or powder form, comprising at least one anhydrous chemical oxidizing agent, preferably in paste or powder form; it being understood that the oxidizing composition is in one of the cavities defined by the envelope i).

19 Claims, 2 Drawing Sheets

(51) Int. Cl.
*A61K 8/22* (2006.01)
*A61K 8/23* (2006.01)
*A61K 8/02* (2006.01)
*A61Q 5/08* (2006.01)
*A61K 8/81* (2006.01)
*A61K 8/25* (2006.01)
*A61K 8/42* (2006.01)
*B65D 65/46* (2006.01)
*A45D 19/00* (2006.01)

(52) U.S. Cl.
CPC .................. *A61K 8/22* (2013.01); *A61K 8/23* (2013.01); *A61K 8/25* (2013.01); *A61K 8/42* (2013.01); *A61K 8/731* (2013.01); *A61K 8/8123* (2013.01); *A61K 8/8129* (2013.01); *A61Q 5/08* (2013.01); *B65D 65/46* (2013.01); *A45D 19/0066* (2021.01); *A45D 2200/1036* (2013.01); *A45D 2200/1045* (2013.01); *A61K 2800/31* (2013.01); *A61K 2800/4322* (2013.01); *A61K 2800/87* (2013.01)

(56) References Cited

U.S. PATENT DOCUMENTS

| | | | |
|---|---|---|---|
| 3,524,842 A | 8/1970 | Grossmann et al. |
| 3,578,386 A | 5/1971 | Kalopissis et al. |
| 3,589,978 A | 6/1971 | Kamal et al. |
| 3,617,163 A | 11/1971 | Kalopissis et al. |
| 3,665,036 A | 5/1972 | Kalopissis et al. |
| 3,817,698 A | 6/1974 | Kalopissis et al. |
| 3,867,456 A | 2/1975 | Kalopissis et al. |
| 3,869,454 A | 3/1975 | Ang et al. |
| 3,955,918 A | 5/1976 | Lang |
| 3,985,499 A | 10/1976 | Lang et al. |
| 4,003,699 A | 1/1977 | Rose et al. |
| 4,017,460 A | 4/1977 | Tessler |
| 4,025,301 A | 5/1977 | Lang |
| 4,151,162 A | 4/1979 | Lang et al. |
| 4,153,065 A | 5/1979 | Lang |
| 4,157,388 A | 6/1979 | Christiansen |
| RE30,199 E | 1/1980 | Rose et al. |
| 4,217,914 A | 8/1980 | Jacquet et al. |
| 4,226,784 A | 10/1980 | Kalopissis et al. |
| 4,348,202 A | 9/1982 | Grollier et al. |
| 4,390,689 A | 6/1983 | Jacquet et al. |
| 4,422,853 A | 12/1983 | Jacquet et al. |
| 4,579,732 A | 4/1986 | Grollier et al. |
| 4,702,906 A | 10/1987 | Jacquet et al. |
| 4,719,282 A | 1/1988 | Nadolsky et al. |
| 4,777,040 A | 10/1988 | Grollier et al. |
| 4,886,517 A | 12/1989 | Bugaut et al. |
| 4,948,579 A | 8/1990 | Jacquet et al. |
| 4,970,066 A | 11/1990 | Grollier et al. |
| 5,008,093 A | 4/1991 | Merianos |
| 5,008,106 A | 4/1991 | Merianos et al. |
| 5,061,289 A | 10/1991 | Clausen et al. |
| 5,077,047 A | 12/1991 | Biss et al. |
| 5,183,901 A | 2/1993 | Login et al. |
| 5,196,189 A | 3/1993 | Jacquet et al. |
| 5,380,340 A | 1/1995 | Neunhoeffer et al. |
| 5,455,340 A | 10/1995 | Bernard et al. |
| 5,534,267 A | 7/1996 | Neunhoeffer et al. |
| 5,663,366 A | 9/1997 | Neunhoeffer et al. |
| 5,674,436 A | 10/1997 | Breitenbach et al. |
| 5,708,151 A | 1/1998 | Möckli |
| 5,753,770 A | 5/1998 | Breitenbach et al. |
| 5,766,576 A | 6/1998 | Löwe et al. |
| 5,780,418 A | 7/1998 | Niinaka et al. |
| 5,879,413 A | 3/1999 | Pengilly et al. |
| 5,888,252 A | 3/1999 | Möckli |
| 5,919,273 A | 7/1999 | Rondeau et al. |
| 5,944,360 A | 8/1999 | Crapart |
| 5,945,032 A | 8/1999 | Breitenbach et al. |
| 5,993,490 A | 11/1999 | Rondeau et al. |
| 6,045,591 A | 4/2000 | Deneulenaere |
| 6,099,592 A | 8/2000 | Vidal et al. |
| 6,120,698 A | 9/2000 | Rounds et al. |
| 6,136,042 A | 10/2000 | Maubru |
| 6,179,881 B1 | 1/2001 | Henrion et al. |
| 6,284,003 B1 | 9/2001 | Rose et al. |
| 6,312,677 B1 | 11/2001 | Millequant et al. |
| 6,338,741 B1 | 1/2002 | Vidal et al. |
| 6,458,167 B1 | 10/2002 | Genet et al. |
| 6,492,502 B2 | 12/2002 | Henrion et al. |
| 6,645,258 B2 | 11/2003 | Vidal et al. |
| 6,730,789 B1 | 5/2004 | Birault et al. |
| 6,797,013 B1 | 9/2004 | Lang et al. |
| 6,863,883 B1 | 3/2005 | Tsujino et al. |
| 7,799,095 B2 | 9/2010 | Mario et al. |
| 9,114,088 B2 | 8/2015 | Konno et al. |
| 10,117,811 B2 | 11/2018 | Aubert et al. |
| 10,130,829 B2 | 11/2018 | Auvert et al. |
| 2001/0001332 A1 | 5/2001 | Henrion et al. |
| 2002/0050013 A1 | 5/2002 | Vidal et al. |
| 2002/0165368 A1 | 11/2002 | Henrion et al. |
| 2003/0019051 A9 | 1/2003 | Vidal et al. |
| 2004/0152610 A1 | 8/2004 | Engel et al. |
| 2006/0002965 A1 | 1/2006 | Hoeffkes et al. |
| 2006/0210499 A1* | 9/2006 | Hoeffkes .................. A61K 8/25 424/62 |
| 2007/0134481 A1 | 6/2007 | Aubrun-Sonneville |
| 2008/0263786 A1 | 10/2008 | Schmenger et al. |
| 2009/0056039 A1 | 3/2009 | Schmenger et al. |
| 2009/0151087 A1 | 6/2009 | Mario et al. |
| 2010/0064449 A1 | 3/2010 | Khan et al. |
| 2011/0033509 A1 | 2/2011 | Simon |
| 2011/0203604 A1 | 8/2011 | Hasegawa et al. |
| 2012/0207689 A1 | 8/2012 | Konno et al. |
| 2017/0007856 A1 | 1/2017 | Aubert et al. |

FOREIGN PATENT DOCUMENTS

| | | |
|---|---|---|
| DE | 2538363 A1 | 5/1976 |
| DE | 19613941 A1 | 10/1977 |
| DE | 3843892 A1 | 6/1990 |
| DE | 4133957 A1 | 4/1993 |
| DE | 4137005 A1 | 5/1993 |
| DE | 4220388 A1 | 12/1993 |
| DE | 4344131 A1 | 6/1995 |
| DE | 19543988 A1 | 5/1997 |
| DE | 19545380 A1 | 6/1997 |
| EP | 0557203 A1 | 8/1993 |
| EP | 0636716 A1 | 2/1995 |
| EP | 0714919 A2 | 6/1996 |
| EP | 0714954 A2 | 6/1996 |
| EP | 0770375 A1 | 5/1997 |
| EP | 0832846 A2 | 4/1998 |
| EP | 0850636 A1 | 7/1998 |
| EP | 0850637 A1 | 7/1998 |
| EP | 0860636 A1 | 8/1998 |
| EP | 0918053 A1 | 5/1999 |
| EP | 0920856 A1 | 6/1999 |
| EP | 1062940 A1 | 12/2000 |
| EP | 1133967 A1 | 9/2001 |
| EP | 1133975 A2 | 9/2001 |
| EP | 2011474 A1 | 1/2009 |
| FR | 1221122 A | 5/1960 |
| FR | 1516943 A | 3/1968 |
| FR | 1540423 A | 9/1968 |
| FR | 1560664 A | 3/1969 |
| FR | 1567219 A | 5/1969 |
| FR | 2189006 A1 | 1/1974 |
| FR | 2270846 A1 | 12/1975 |
| FR | 2275462 A1 | 1/1976 |
| FR | 2285851 A1 | 4/1976 |
| FR | 2459044 A | 1/1981 |
| FR | 2570946 A1 | 4/1986 |
| FR | 2733749 A1 | 11/1996 |
| FR | 2757385 A1 | 6/1998 |
| FR | 2788433 A1 | 7/2000 |
| FR | 2801308 A1 | 5/2001 |
| FR | 2998146 A1 | 5/2014 |

(56) References Cited

FOREIGN PATENT DOCUMENTS

| GB | 195386 A | 2/1924 |
|---|---|---|
| GB | 738585 A | 10/1955 |
| GB | 1026978 A | 4/1966 |
| GB | 1153196 A | 5/1969 |
| GB | 1163385 A | 9/1969 |
| GB | 1514466 A | 6/1978 |
| JP | 02-019576 A | 1/1990 |
| JP | 05-163124 A | 6/1993 |
| JP | 2010-501032 A | 1/2010 |
| JP | 2014-501339 A | 1/2014 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 97/44004 A1 | 11/1997 |
| WO | 99/48465 A1 | 9/1999 |
| WO | 01/66646 A1 | 9/2001 |
| WO | 03/029359 A1 | 4/2003 |
| WO | 03/044152 A1 | 5/2003 |
| WO | 2011/059027 A1 | 5/2011 |
| WO | 2012/015034 A1 | 2/2012 |
| WO | 2015/097098 A1 | 7/2015 |
| WO | 2015/097099 A1 | 7/2015 |
| WO | 2015/097101 A1 | 7/2015 |

OTHER PUBLICATIONS

International Search Report for counterpart Application No. PCT/EP2014/078851, dated Mar. 25, 2015.
International Search Report for counterpart Application No. PCT/EP2014/078848, dated Mar. 25, 2015.
International Search Report for counterpart Application No. PCT/EP2014/078855, dated Mar. 27, 2015.
Porter, M.R., "Handbook of Surfactants," published by Blackie & Son (Glasgow and London), 1991, pp. 116-178.
"Textile Auxiliaries," Ullmann's Encyclopedia of Industrial Chemistry, 2002, Wiley-VCH Verlag Gmbh & Co. KGaA, Weinheim, 10.1002/14356007.a26 227, pp. 1-129.
"Azo Dyes," Ullman's Encyclopedia of Industrial Chemistry, 2005, Wiley-VCH Verlag GmbH & col. KGaA, Weinheim 10.1002/1436007.a03 245, point 3.2, pp. 1-93.
Ashford's Dictionary of Industrial Chemicals, Second Edition, 2001, pp. 14-39.
Non-Final Office Action for U.S. Appl. No. 15/107,289, dated Apr. 27, 2017 (now U.S. Pat. No. 10,117,811).
Final Office Action for U.S. Appl. No. 15/107,289, dated Nov. 13, 2017 (now U.S. Pat. No. 10,117,811).
Non-Final Office Action for U.S. Appl. No. 15/107,258, dated Apr. 27, 2017 (now U.S. Pat. No. 10,130,829).
Final Office Action for U.S. Appl. No. 15/107,258, dated Nov. 9, 2017 (now U.S. Pat. No. 10,130,829).
Non-Final Office Action for copending U.S. Appl. No. 15/107,319, dated Apr. 16, 2018.
Final Office Action for copending U.S. Appl. No. 15/107,319, dated Nov. 14, 2018.
Non-Final Office Action for copending U.S. Appl. No. 15/107,319, dated Oct. 31, 2019.

* cited by examiner

PROCESS FOR TREATING KERATIN FIBERS USING A PACKAGING ARTICLE COMPRISING AN ENVELOPE AND AN ANHYDROUS COMPOSITION COMPRISING AN OXIDIZING AGENT

CROSS REFERENCE TO RELATED APPLICATION

This is a continuation of application Ser. No. 15/107,319 filed on Jun. 22, 2016, which is a national stage application of PCT/EP2014/078855, filed on Dec. 19, 2014, which claims priority to French Application No. 1363394, filed on Dec. 23, 2013, all of which are incorporated by reference herein by their entireties.

The present invention relates to a process for treating keratinic fibers using a packaging article comprising an anhydrous chemical oxidizing agent for dyeing and/or bleaching keratin fibres, in particular human hair.

In cosmetics, oxidizing compositions are used in the fields of dyeing, bleaching and permanently reshaping keratin fibres, and in particular human keratin fibres such as the hair.

Thus, in the oxidation dyeing of the hair, oxidizing compositions are mixed with oxidation dyes (bases and couplers), which are colourless in themselves, to generate coloured compounds and dyes by a process of oxidative condensation. Oxidizing compositions are also used in the direct dyeing of the hair as a mixture with certain direct dyes that are coloured and colouring, in order to obtain a colouring with a lightening effect on the hair. Among the oxidizing agents conventionally used for dyeing keratin fibres, mention may be made of hydrogen peroxide or compounds that are capable of producing hydrogen peroxide by hydrolysis, such as urea peroxide. Persalts such as perborates and persulfates may also be used.

In hair bleaching, bleaching compositions contain one or more oxidizing agents. Among these oxidizing agents, the ones most conventionally used are hydrogen peroxide or compounds that are capable of producing hydrogen peroxide by hydrolysis, such as urea peroxide or persalts such as perborates, percarbonates and persulfates, hydrogen peroxide and persulfates being particularly preferred.

These compositions may be aqueous compositions containing alkaline agents (amines or aqueous ammonia) that are diluted at the time of use with an aqueous hydrogen peroxide composition.

These compositions may also be formed from anhydrous products, which are powders or pastes, and which contain alkaline compounds (amines and/or alkaline silicates), and a peroxygenated reagent such as ammonium or alkali metal persulfates, perborates or percarbonates, which is diluted at the time of use with an aqueous hydrogen peroxide composition.

However, bleaching powders have a tendency to form dust during their handling, transportation and storage.

Now, the products of which they are composed (alkali metal persulfates and silicates) are aggressive and in particular irritant to the eyes, the respiratory pathways and mucous membranes.

To overcome the problem of volatility of the bleaching powders, less volatile powders have been developed by adding additives for reducing the content of fine particles, and pastes have been developed comprising the said pulverulent agents (peroxygenated salts, alkaline agents, thickeners) in an organic inert liquid support. However, these less volatile powders and these pastes may prove to be less effective than the simple starting powders. Moreover, pastes, just like powders, nevertheless require certain precautions during their handling, especially as regards weighing them out in order to mix them with the oxidizing composition, so as to avoid staining clothing.

In addition, it is sought to improve the ease of mixing and of application of dye compositions or bleaching compositions in powder or paste form, which are mixed at the time of use with the aqueous oxidizing composition.

The aim of the present invention is to provide a process for treating keratin fibres, in particular for dyeing and/or bleaching keratin fibres, which can solve the problems, in particular the handling problems, of the known compositions of the prior art, by using an article comprising an envelope and an anhydrous oxidizing composition. This article makes it possible to avoid the handling problems linked to the volatility of the powders or the weighing-out problems by proposing a ready-to-use product, without a step of metering out. It also makes it possible to improve the resistance of the oxidizing composition to temperature variations, and in particular makes it possible to avoid the problem of destabilization on storage at low temperatures and during transportation including temperature cycles. It also makes it possible to avoid losses of lightening power.

Another object of the present invention is to propose oxidizing compositions for keratin fibres that are easy to mix and to apply and that in particular allow homogeneous distribution of the composition over the hair.

This/these aim(s) are achieved by the present invention, one subject of which is a process for treating keratin fibres, especially human keratin fibres such as the hair using a packaging article comprising:
i) an envelope defining at least one cavity, the envelope comprising water-soluble and/or liposoluble fibres, preferably water-soluble fibres;
ii) at least one anhydrous oxidizing composition, preferably in paste or powder form, comprising at least one anhydrous chemical oxidizing agent, preferably in paste or powder form;

it being understood that the oxidizing composition is in one of the cavities defined by the envelope i).

According to an embodiment, the process of the invention comprises the following steps: i) mixing the packaging article as defined previously with a composition that is capable of dissolving the packaging article, ii) applying the resulting composition to the keratin fibres, iii) leaving the composition to stand on the fibres, iv) rinsing the said fibres, v) optionally shampooing the fibres, rinsing them and drying them, the composition that is capable of dissolving the packaging article possibly containing a chemical oxidizing agent.

Another subject of the invention is the use of the packaging article as defined previously for dyeing, lightening and/or bleaching keratin fibres, preferably the hair.

The use of the packaging article makes it possible to obtain compositions whose consistency is pleasant on use, which are easy to mix and to apply and which do not run outside the areas to be treated.

When it is used in a dyeing process, the article makes it possible to obtain a colouring that shows excellent dyeing properties, especially in terms of chromaticity, selectivity, intensity or persistence, which are identical to, comparable to or even better than those of the standard packaging compositions, i.e. which are in separated liquid form, and/or good lightening properties on keratin fibres.

When it is used in a bleaching process, it makes it possible to obtain good intensity and homogeneity of bleaching.

In addition, the packaging article of the invention makes it possible for there no longer to be direct contact between the user and the powdered ingredients. Moreover, the packaging article has a size that is reduced to its strict minimum, very compact, without bulky packaging.

According to one embodiment, the article makes it possible to avoid the use of separate bleaching, oxidizing and alkaline compositions and to reduce the number of steps of the dyeing and/or bleaching process.

Other characteristics and advantages of the invention will emerge more clearly on reading the description and the examples that follow.

BRIEF DESCRIPTION OF THE FIGURES

FIG. 1b shows a top view of the exemplary embodiment in FIG. 1a.

DETAILED DESCRIPTION

Figure 1A:
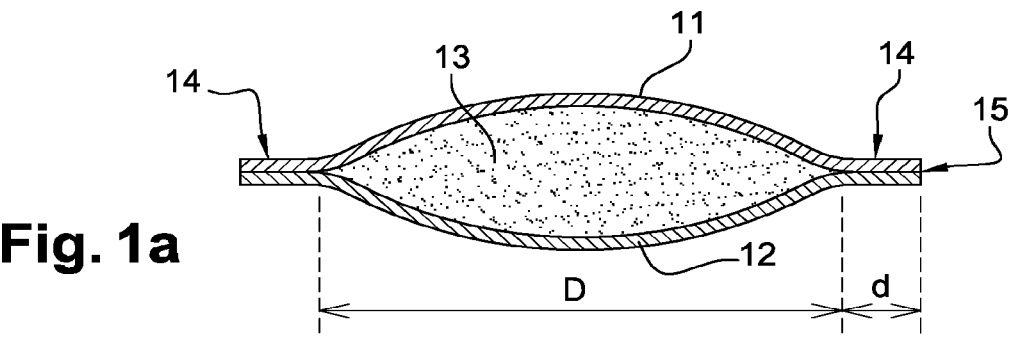
FIG. 1a shows a cross section of an exemplary embodiment of a packaging article according to the disclosure.

In the text hereinbelow, and unless otherwise indicated, the limits of a range of values are included within that range.

The expression "at least one" is equivalent to the expression "one or more".

A composition is said to be "anhydrous" when it comprises a water content of not more than 3% by weight and preferably not more than 1% by weight relative to the weight of the composition. Preferably, this water content is not more than 0.5% by weight relative to the weight of the anhydrous composition. More particularly, the water content ranges from 0 to 1% by weight and preferably from 0 to 0.5% by weight relative to the total weight of the composition.

The term "anhydrous paste" means an anhydrous composition with a viscosity of greater than 5 poises and preferably greater than 10 poises, measured at 25° C. and at a shear rate of 1 s$^{-1}$; this viscosity being able to be determined using a cone-plate rheometer.

The term "in anhydrous powder form" means an anhydrous composition or ingredient in pulverulent form, which is preferably substantially free of dust (or fine particles). In other words, the particle size distribution of the particles is such that the weight ratio of particles less than or equal to 100 micrometres in size (fines content) and preferably less than or equal to 65 micrometres in size (fines content) is advantageously less than or equal to 5%, preferably less than 2% and more particularly less than 1% (particle size evaluated using a Retsch AS 200 Digit particle size analyser; oscillation height: 1.25 mm/screening time: 5 minutes). Advantageously, the particle size is between 100 μm and 3 mm and more particularly between 65 μm and 2 mm.

According to a preferred embodiment of the invention, the anhydrous oxidizing composition is in paste or powder form and is introduced into the cavity formed by the envelope. The envelope may consist of a lap (e.g., layer) consisting of water-soluble and/or liposoluble fibres and which is folded on itself, or alternatively the envelope may consist of a first lap which is covered with a second lap also consisting of water-soluble and/or liposoluble fibres, and the lap is then folded on itself or the two laps are then hermetically assembled so that the pastes or powders cannot diffuse out, the pastes or powders thus being hermetically enveloped by the envelope i).

The term "water-soluble" means soluble in water, in particular in a proportion of at least 10 grams per litre of water, preferably at least 20 g/l and better still at least 50 g/l, at a temperature of less than or equal to 35° C.

The term "liposoluble" means soluble in a liquid fatty substance as defined for ingredient vi) below, in particular in a proportion of at least 10 grams per litre of liquid fatty substance, in particular in a plant oil or mineral oil such as liquid petroleum jelly, preferably at least 20 g/l in a liquid fatty substance, better still at least 50 g/l in a fatty substance, at a temperature of less than or equal to 35° C.

The term "temperature of less than or equal to 35° C." means a temperature not exceeding 35° C. and preferably greater than or equal to 0° C., for example ranging from more than 1.0° C. to 35° C., better still from 5° C. to 30° C. and even better still from 10° C. to 30° C. or 10° C. to 20° C. It is understood that all the temperatures are given at atmospheric pressure.

The packaging article used in the process according to the invention is preferably water-soluble at a temperature of less than or equal to 35° C.

i) An Envelope Comprising Water-Soluble and/or Liposoluble Fibres

The packaging article used in the process according to the invention comprises an envelope which defines at least one cavity, the cavity(ies) containing at least one anhydrous oxidizing composition, the packaging article optionally containing at least one alkaline agent in one of its cavities. The packaging article preferably comprises only one cavity.

The envelope of the article comprises one or more laps of water-soluble and/or liposoluble fibres and one or more cavities containing the anhydrous oxidizing composition, the oxidizing composition being separate from the lap or from the envelope. Such an envelope is different from water-soluble or liposoluble thin films in which the oxidizing composition would be incorporated in the lap(s) forming the envelope. Relative to these water-soluble or liposoluble thin films, the envelope according to the invention has the advantage of allowing the incorporation of constituents that are incompatible therewith, and of being simpler to use since it does not require any premixing or any dissolution in a solvent of the constituents, or any heating to evaporate the solvent. The process for manufacturing the packaging article of the invention is also faster and less expensive than the process for manufacturing thin films.

Furthermore, when the active agents, in this case in particular the oxidizing agents, are used in dispersion to form a thin film, this may give rise to compatibility problems and mechanical problems (breaking of the film) and may impose limits on the concentration of active agents. In addition, the envelope and the laps that are useful for the invention have the advantage of allowing wider diversity in the choice of the shape and appearance of the article, since the water-soluble and/or liposoluble lap(s) may have a variable thickness and a variable density, giving access to a wide variety of shapes and sizes, whereas the thin film is difficult to dry if the thickness is too large, and it is fragile and difficult to manipulate if the size is too large.

Advantageously, the envelope or the laps are "touch-deformable", which especially means that the envelope and the laps become deformed when they are held and pinched between a users fingers.

Preferably, the anhydrous oxidizing composition in powder or paste form is present in a cavity generated by at least two laps constituting the envelope and defining between them a cavity, the said laps preferably comprising water-soluble fibres.

According to a particular embodiment of the invention, at least one of the laps of the packaging article consists predominantly and preferably exclusively of water-soluble fibres, and more preferentially all the laps of the packaging article of the invention consist exclusively of water-soluble fibres, preferably water-soluble at a temperature of less than or equal to 30° C.

Preferably, the envelope i) predominantly comprises water-soluble polymer fibres. More particularly the envelope i) comprises natural, artificial or synthetic water-soluble polymer fibres, preferably chosen from polyvinyl alcohol (PVA) fibres, polysaccharide fibres such as cellulose and more specifically hydroxyalkylcelluloses, polylactic acid fibres and polyalkylene oxide fibres, and mixtures thereof; more preferably selected from PVA and hydroxyl($C_1$-$C_6$)alkylcelluloses.

The term "fibre" means any object whose length is greater than its cross-section. In other words, it should be understood as meaning an object of length L and of diameter D such that L is greater and preferably very much greater (i.e. at least three times greater) than D, D being the diameter of the circle in which the cross section of the fibre is inscribed. In particular, the ratio L/D (or aspect ratio) is chosen in the range from 3.5 to 2500, preferably from 5 to 500 and better still from 5 to 150. The cross-section of a fibre may have any round, toothed or fluted shape, or alternatively a bean shape, but also multilobate, in particular trilobate or pentalobate, X-shaped, ribbon-shaped, square, triangular, elliptical or the like. The fibres of the invention may or may not be hollow. The fibres used according to the present invention may be of natural, synthetic or even artificial origin. Advantageously, the said fibres are of synthetic origin.

A "natural fibre" is by definition a fibre that is naturally present in nature, directly or after mechanical and/or physical treatment. Fibres of animal origin such as cellulose fibres, in particular extracted from wood, plants or algae, and rayon fibres, are collated in this category.

The "artificial fibres" are either totally synthetic or derived from natural fibres that have been subjected to one or more chemical treatments in order especially to improve their mechanical and/or physicochemical properties.

The "synthetic fibres" collate fibres obtained by chemical synthesis and are generally fibres consisting of one or more mono-component or multi-component, composite or non-composite polymers and/or copolymers, which are generally extruded and/or drawn to the desired diameter of the fibre.

Preferably, the fibres of the invention consist of one or more water-soluble polymers.

The water-soluble polymer(s) of the invention contain water-soluble units in their backbones. The water-soluble units are obtained from one or more water-soluble monomers.

The term "water-soluble monomer" means a monomer whose solubility in water is greater than or equal to 1% and preferably greater than or equal to 5% at 25° C. and at atmospheric pressure (760 mmHg).

The said synthetic water-soluble polymer(s) used in the context of the present invention are advantageously obtained from water-soluble monomers comprising at least one double bond. These monomers may be chosen from cationic, anionic and nonionic monomers, and mixtures thereof.

As water-soluble monomers that may be used as precursors of the water-soluble units, alone or as a mixture, examples that may be mentioned include the following monomers, which may be in free or salified form:
(meth)acrylic acid,
styrenesulfonic acid,
vinyl sulfonic acid and (meth)allylsulfonic acid,
vinylphosphonic acid,
N-vinylacetamide and N-methyl-N-vinylacetamide,
N-vinylformamide and N-methyl-N-vinylformamide,
N-vinyllactams comprising a cyclic alkyl group containing from 4 to 9 carbon atoms, such as N-vinylpyrrolidone, N-butyrolactam and N-vinylcaprolactam,
maleic anhydride,
itaconic acid,
vinyl alcohol of formula $CH_2{=}CHOH$,
vinyl ethers of formula $CH_2{=}CHOR$ in which R is a linear or branched, saturated or unsaturated hydrocarbon-based radical containing from 1 to 6 carbons,
dimethyldiallylammonium halides (chloride),
quaternized dimethylaminoethyl methacrylate (DMAEMA),
(meth)acrylamidopropyltrimethylammonium halides (chloride) (APTAC and MAPTAC),
methylvinylimidazolium halides (chloride),
2-vinylpyridine and 4-vinylpyridine,
acrylonitrile,
glycidyl (meth)acrylate,
vinyl halides (chloride) and vinylidene chloride,
vinyl monomers of formula (I) below:

$$H_2C{=}C(R){-}C(O){-}X \qquad (I)$$

in which formula (I):
R is chosen from H and ($C_1$-$C_6$)alkyl such as methyl, ethyl and propyl;
X is chosen from:
alkoxy of —OR' type in which R' is a linear or branched, saturated or unsaturated hydrocarbon-based radical containing from 1 to 6 carbons, optionally substituted with at least one halogen atom (iodine, bromine, chlorine or fluorine); a sulfonic (—$SO_3$), sulfate (—$SO_4^-$), phosphate (—$PO_4H_2$); hydroxyl (—OH); primary amine (—$NH_2$); secondary amine (—$NHR_6$), tertiary amine (—$NR_6R_7$) or quaternary amine (—$N^+R_6R_7R_8$) group with $R_6$, $R_7$ and $R_8$ being, independently of each other, a linear or branched, saturated or unsaturated hydrocarbon-based radical containing 1 to 6 carbon atoms, with the proviso that the sum of the carbon atoms of R'+$R_6$+$R_7$+$R_8$ does not exceed 6;
groups —$NH_2$, —NHR' and —NR'R" in which R' and R" are, independently of each other, linear or branched, saturated or unsaturated hydrocarbon-based radicals containing 1 to 6 carbon atoms, with the proviso that the total number of carbon atoms of R'+R" does not exceed 6, the said R' and R" being optionally substituted with a halogen atom (iodine, bromine, chlorine or fluorine); a hydroxyl (—OH); sulfonic (—$SO_3^-$); sulfate (—$SO_4^-$); phosphate (—$PO_4H_2$); primary amine (—$NH_2$); secondary amine (—$NHR_6$), tertiary amine (—$NR_6R_7$) and/or quaternary amine (—$N^+R_6R_7R_8$) group with $R_6$, $R_7$ and $R_8$ being, independently of each other, a linear or branched, saturated or unsaturated hydrocarbon-based radical containing 1 to 6 carbon atoms, with the proviso that the sum of the carbon atoms of R'+R"+$R_6$+$R_7$+$R_8$ does not exceed 6. As compounds corresponding to this formula, examples that may be mentioned include N,N-dimethylacrylamide and N,N-diethylacrylamide;

and mixtures thereof.

Anionic monomers that may especially be mentioned include (meth)acrylic acid, acrylamido-2-methylpropanesulfonic acid, itaconic acid and alkali metal, alkaline-earth metal or ammonium salts thereof or salts thereof derived from an organic amine such as an alkanolamine.

Nonionic monomers that may especially be mentioned include (meth)acrylamide, N-vinylformamide, N-vinylacetamide, hydroxypropyl (meth)acrylate and the vinyl alcohol of formula $CH_2=CHOH$.

The cationic monomers are preferably chosen from quaternary ammonium salts derived from a diallylamine and those corresponding to formula (II) below:

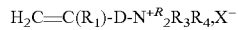

in which formula (II):
$R_1$ represents a hydrogen atom or a methyl group,
$R_2$ and $R_3$, which may be identical or different, represent a hydrogen atom or a linear or branched $C_1$-$C_4$ alkyl group,
$R_4$ represents a hydrogen atom, a linear or branched $C_1$-$C_4$ alkyl group or an aryl group
D represents the following divalent unit: —$(Y)_n$-(A)- in which:
Y represents an amide function, an ester (O—C(O) or C(O)—O), a urethane or a urea,
A represents a linear or branched, cyclic or acyclic $C_1$-$C_{10}$ alkylene group, which may be substituted or interrupted with a divalent aromatic or heteroaromatic group. The alkylene groups may be interrupted with an oxygen atom, a nitrogen atom, a sulfur atom or a phosphorus atom; the alkylene may be interrupted with a ketone function, an amide, an ester (O—C(O) or C(O)—O), a urethane or a urea,
n is an integer ranging from 0 to 1,
$X^-$ represents an anionic counterion, for instance a chloride or a sulfate.

Examples of water-soluble cationic monomers that may especially be mentioned include the following compounds, and also salts thereof: dimethylaminoethyl, (meth)acryloyloxyethyltrimethylammonium, (meth)acryloyloxyethyldimethylbenzylammonium, N-[dimethylaminopropyl](meth)acrylamide, (meth)acrylamidopropyltrimethylammonium, (meth)acrylamidopropyldimethylbenzylammonium and dimethylaminohydroxypropyl (meth)acrylate, (meth)acryloyloxyhydroxypropyltrimethylammonium, (meth)acryloyloxyhydroxypropyldimethylbenzylammonium and dimethyldiallylammonium (meth)acrylate.

Preferably, the polymer according to the invention is polymerized from at least one cationic monomer as defined above.

Preferably, the polymers are polymerized from the following monomers comprising at least one double bond:
0 to 30 mol % of acrylic acid,
0 to 95.5 mol % of acrylamide, and
0.5 mol % to 100 mol % of at least one cationic monomer represented in formula (II) as defined above.

As polymers that are particularly preferred in the invention, mention may be made especially of those polymerized from
10% of acryloyloxyethyldimethylbenzylammonium chloride and 90% of acrylamide, 30% of acryloyloxytrimethylammonium chloride, 50% of acryloyloxyethyldimethylbenzylammonium chloride and 20% of acrylamide,
10% of acryloyloxyethyltrimethylammonium chloride and 90% of acrylamide,
30% of diallyldimethylammonium chloride and 70% of acrylamide,
30% of acrylic acid and 70% of acrylamide.

According to a particular embodiment, the polymers are polymerized from a cationic monomer and acrylic acid, the number of moles of the cationic monomer being greater than the number of moles of acrylic acid.

As water-soluble polymers derived from natural products, mention may be made of polysaccharides, i.e. polymers bearing sugar units.

The term "sugar unit" means a unit derived from a carbohydrate of formula $C_n(H_2O)_{n-1}$ or $(CH_2O)_n$, which may be optionally modified by substitution and/or by oxidation and/or by dehydration. The sugar units that may be included in the composition of the polymers of the invention are preferably derived from the following sugars: glucose, galactose, arabinose, rhamnose, mannose, xylose, fucose, fructose, anhydrogalactose, galacturonic acid, glucuronic acid, mannuronic acid, galactose sulfate, anhydrogalactose sulfate.

The polymers bearing sugar units according to the invention may be of natural or synthetic origin. They may be nonionic, anionic, amphoteric or cationic. The base units of the polymers bearing sugar units of the invention may be monosaccharides or disaccharides.

As polymers that may be used, mention may be made especially of the following native gums, and also derivatives thereof:
a) tree or shrub exudates, including:
gum arabic (branched polymer of galactose, arabinose, rhamnose and glucuronic acid);
ghatti gum (polymer derived from arabinose, galactose, mannose, xylose and glucuronic acid);
karaya gum (polymer derived from galacturonic acid, galactose, rhamnose and glucuronic acid);
gum tragacanth (or tragacanth) (polymer of galacturonic acid, galactose, fucose, xylose and arabinose);
b) gums derived from algae, including:
agar (polymer derived from galactose and anhydrogalactose);
alginates (polymers of mannuronic acid and of glucuronic acid);
carrageenans and furcellerans (polymers of galactose sulfate and of anhydrogalactose sulfate);
c) gums derived from seeds or tubers, including:
guar gum (polymer of mannose and galactose);
locust bean gum (polymer of mannose and galactose);
fenugreek gum (polymer of mannose and galactose);
tamarind gum (polymer of galactose, xylose and glucose);
konjac gum (polymer of glucose and mannose) in which the main constituent is glucomannan, a polysaccharide of high molecular weight (500 000<$M_{glucomannan}$<2 000 000) composed of D-mannose and D-glucose units with branches every 50 or 60 units approximately;
d) microbial gums, including:
xanthan gum (polymer of glucose, mannose acetate, mannose/pyruvic acid and glucuronic acid);
gellan gum (polymer of partially acylated glucose, rhamnose and glucuronic acid);
scleroglucan gum (glucose polymer);
biosaccharide gum (polymer of galacturonic acid, fucose and D-galactose), for example the product sold under the name Fucogel 1.5P from Solabia (polysaccharide rich in fucose (20%) at 1.1% in stabilized water (1.5% phenoxyethanol));

e) plant extracts, including:
cellulose (glucose polymer);
starch (glucose polymer);
inulin (polymer of fructose and glucose).

These polymers may be physically or chemically modified. A physical treatment that may especially be mentioned is the temperature. Chemical treatments that may be mentioned include esterification, etherification, amidation or oxidation reactions. These treatments can lead to polymers that may be nonionic, anionic, cationic or amphoteric.

Preferably, these chemical or physical treatments are applied to guar gums, locust bean gums, starches and celluloses.

The nonionic guar gums that may be used according to the invention may be modified with $C_1$-$C_6$ hydroxyalkyl groups. Among the hydroxyalkyl groups that may be mentioned are hydroxymethyl, hydroxyethyl, hydroxypropyl and hydroxybutyl groups.

These guar gums are well known in the prior art and may be prepared, for example, by reacting the corresponding alkene oxides, for instance propylene oxides, with the guar gum so as to obtain a guar gum modified with hydroxypropyl groups.

The degree of hydroxyalkylation preferably ranges from 0.4 to 1.2, and corresponds to the number of alkylene oxide molecules consumed by the number of free hydroxyl functions present on the guar gum.

Such nonionic guar gums optionally modified with hydroxyalkyl groups are sold, for example, under the trade names Jaguar HP8, Jaguar HP60 and Jaguar HP120 by the company Rhodia Chimie.

The guar gums modified with cationic groups that may be used more particularly according to the invention are guar gums comprising trialkylammonium cationic groups. Preferably, 2% to 30% by number of the hydroxyl functions of these guar gums bear trialkylammonium cationic groups. Even more preferentially, 5% to 20% of the number of the hydroxyl functions of these guar gums are branched with trialkylammonium cationic groups. Among these trialkylammonium groups, mention may be made most particularly of trimethylammonium and triethylammonium groups. Even more preferentially, these groups represent from 5% to 20% by weight relative to the total weight of the modified guar gum.

According to the invention, use may be made of guar gums modified with 2,3-epoxypropyltrimethylammonium chloride.

These guar gums modified with cationic groups are products already known per se and are, for example, described in patents U.S. Pat. No. 3,589,578 and US 4 0131 307. Such products are moreover sold especially under the trade names Jaguar C13 S, Jaguar C 15 and Jaguar C 17 by the company Rhodia Chimie.

A modified locust bean gum that may be used is cationic locust bean gum containing hydroxypropyltrimonium groups, such as Catinal CLB 200 sold by the company Toho.

The starch molecules used in the present invention may originate from any plant source of starch, especially cereals and tubers; more particularly, they may be starches from corn, rice, cassava, barley, potato, wheat, sorghum, pea, oat or tapioca. It is also possible to use the starch hydrolysates mentioned above. The starch is preferably derived from potato.

The starches may be chemically or physically modified, especially by one or more of the following reactions: pregelatinization, oxidation, crosslinking, esterification, etherification, amidation, heat treatments.

More particularly, these reactions may be performed in the following manner:
pregelatinization by splitting the starch granules (for example drying and cooking in a drying drum);
oxidation with strong oxidizing agents, leading to the introduction of carboxyl groups into the starch molecule and to depolymerization of the starch molecule (for example by treating an aqueous starch solution with sodium hypochlorite);
crosslinking with functional agents capable of reacting with the hydroxyl groups of the starch molecules, which will thus bond together (for example with glyceryl and/or phosphate groups);
esterification in alkaline medium for the grafting of functional groups, especially $C_1$-$C_6$ acyl (acetyl), $C_1$-$C_6$ hydroxyalkyl (hydroxyethyl or hydroxypropyl), carboxymethyl or octenylsuccinic.

Monostarch phosphates (of the type Am—O—PO—(OX)$_2$), distarch phosphates (of the type Am—O—PO—(OX)—O—Am) or even tristarch phosphates (of the type Am—O—PO—(O—Am)$_2$) or mixtures thereof may especially be obtained by crosslinking with phosphorus compounds, Am meaning starch and X especially denoting alkali metals (for example sodium or potassium), alkaline-earth metals (for example calcium or magnesium), ammonia salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Distarch phosphates or compounds rich in distarch phosphate will preferentially be used, for instance the product sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure Zea from National Starch (gelatinized corn distarch phosphate).

A preferred starch is a starch that has undergone at least one chemical modification such as at least one esterification.

According to the invention, amphoteric starches comprising one or more anionic groups and one or more cationic groups may also be used. The anionic and cationic groups may be linked to the same reactive site of the starch molecule or to different reactive sites; they are preferably linked to the same reactive site. The anionic groups may be of carboxylic, phosphate or sulfate type, preferably carboxylic. The cationic groups may be of primary, secondary, tertiary or quaternary amine type.

The amphoteric starches are especially chosen from the compounds having the following formulae:

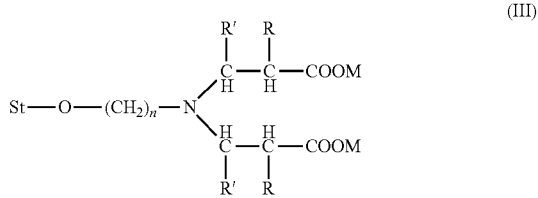

(III)

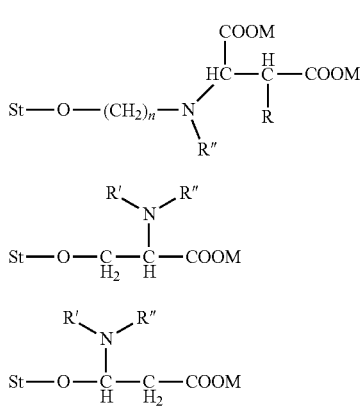

in which formula (III) to (VI):
St-O represents a starch molecule;
R, which may be identical or different, represents a hydrogen atom or a methyl radical;
R', which may be identical or different, represents a hydrogen atom, a methyl radical or a group —C(O)—OH;
n is an integer equal to 2 or 3;
M, which may be identical or different, denotes a hydrogen atom, an alkali metal or alkaline-earth metal such as Na, K or Li, a quaternary ammonium $NH_4$, or an organic amine;
R" represents a hydrogen atom or a $C_1$-$C_{18}$ alkyl radical.

These compounds are especially described in U.S. Pat. Nos. 5,455,340 and 4,017,460.

Use is particularly made of the starches of formula (IV) or (V); and preferentially starches modified with 2-chloroethylaminodipropionic acid, i.e. starches of formula (IV) or (V) in which R, R', R" and M represent a hydrogen atom and n is equal to 2. The preferred amphoteric starch is a starch chloroethylamidodipropionate.

The celluloses and cellulose derivatives may be anionic, cationic, amphoteric or nonionic.

Among these derivatives, cellulose ethers, cellulose esters and cellulose ester ethers are distinguished.

Among the cellulose esters, mention may be made of mineral cellulose esters (cellulose nitrates, sulfates and phosphates), organic cellulose esters (cellulose monoacetates, triacetates, amidopropionates, acetate butyrates, acetate propionates and acetate trimellitates), and mixed organic/mineral cellulose esters, such as cellulose acetate butyrate sulfates and acetate propionate sulfates.

Among the cellulose ester ethers, mention may be made of hydroxypropylmethylcellulose phthalates and ethylcellulose sulfates.

Among the nonionic cellulose ethers that may be mentioned are alkylcelluloses such as methylcelluloses and ethylcelluloses (for example Ethocel Standard 100 Premium from Dow Chemical); hydroxyalkylcelluloses such as hydroxymethylcelluloses and hydroxyethylcelluloses (for example Natrosol 250 HHR sold by Aqualon) and hydroxypropylcelluloses (for example Klucel EF from Aqualon); mixed hydroxyalkyl-alkylcelluloses such as hydroxypropylmethylcelluloses (for example Methocel E4M from Dow Chemical), hydroxyethylmethylcelluloses, hydroxyethylethylcelluloses (for example Bermocoll E 481 FQ from Akzo Nobel) and hydroxybutylmethylcelluloses.

Among the anionic cellulose ethers, mention may be made of carboxyalkylcelluloses and salts thereof. Examples that may be mentioned include carboxymethylcelluloses, carboxymethylmethylcelluloses (for example Blanose 7M from the company Aqualon) and carboxymethylhydroxyethylcelluloses, and also the sodium salts thereof.

Among the cationic cellulose ethers, mention may be made of crosslinked or non-crosslinked, quaternized hydroxyethylcelluloses. The quaternizing agent may especially be diallyldimethylammonium chloride (for example Celquat L200 from National Starch). Another cationic cellulose ether that may be mentioned is hydroxypropyltrimethylammonium hydroxyethyl cellulose (for example Ucare Polymer JR 400 from Amerchol).

Among the associative polymers bearing sugar units, mention may be made of celluloses or derivatives thereof, modified with groups comprising at least one fatty chain, such as alkyl, arylalkyl or alkylaryl groups or mixtures thereof in which the alkyl groups are of $C_8$-$C_{22}$; nonionic alkylhydroxyethylcelluloses such as the products Natrosol Plus Grade 330 CS and Polysurf 67 ($C_{16}$ alkyl) sold by the company Aqualon; quaternized alkylhydroxyethylcelluloses (cationic), such as the products Quatrisoft LM 200, Quatrisoft LM-X 529-18-A, Quatrisoft LM-X 529-18-B ($C_{12}$ alkyl) and Quatrisoft LM-X 529-8 ($C_{18}$ alkyl) sold by the company Amerchol, the products Crodacel QM and Crodacel QL ($C_{12}$ alkyl) and Crodacel QS ($C_{18}$ alkyl) sold by the company Croda, and the product Softcat SL 100 sold by the company Amerchol; nonionic nonoxynylhydroxyethylcelluloses such as the product Amercell HM-1500 sold by the company Amerchol; nonionic alkylcelluloses such as the product Bermocoll EHM 100 sold by the company Berol Nobel.

As associative polymers bearing sugar units derived from guar, mention may be made of hydroxypropyl guars modified with a fatty chain, such as the product Esaflor HM 22 (modified with a $C_{22}$ alkyl chain) sold by the company Lamberti; the product Miracare XC 95-3 (modified with a $C_{14}$ alkyl chain) and the product RE 205-146 (modified with a $C_{20}$ alkyl chain) sold by Rhodia Chimie.

The polymer(s) bearing sugar units of the invention are preferably chosen from guar gums, locust bean gums, xanthan gums, starches and celluloses, in their modified form (derivatives) or unmodified form.

Preferably, the polymers bearing sugar units according to the invention are nonionic.

More preferably, the polymer(s) bearing sugar units of the invention are chosen from modified nonionic guar gums, especially modified with $C_1$-$C_6$ hydroxyalkyl groups.

The polymers described above more particularly have a weight-average molecular weight of greater than 1 000 000 and preferably between 1 000 000 and 50 000 000. The molecular weight is determined by the RSV (Reduced Specific Viscosity) method as defined in "Principles of Polymer Chemistry" Cornell University Press, Ithaca, NY 1953 Chapter VII "Determination of molecular weight" pp. 266-316.

The fibres may be spun, carded or twisted. Advantageously, the fibres used in the context of the present invention are spun. The mean diameter of the fibres used according to the present invention, which may be identical or different, is less than 500 µm. Advantageously, such a diameter is less than 200 µm, preferably less than 100 µm or even less than 50 µm.

Mention may be made more particularly of water-soluble fibres that include fibres based on polyvinyl alcohol (PVA), fibres of polysaccharides such as glucomannans, starches or celluloses such as carboxymethylcelluloses, polyalginic acid fibres, polylactic acid fibres and polyalkylene oxide fibres, and also a mixture thereof. More preferentially, the water-soluble fibre(s) used in the invention are chosen from PVA-based fibres.

The fibres of the envelope or of the laps are generally entangled. As indicated above, the term "envelope or lap comprising water-soluble fibres" means an envelope or laps which may consist entirely of water-soluble fibres or a lap which may comprise both water-soluble fibres and fibres that are insoluble in water at a temperature of less than or equal to 35° C., the soluble fibres necessarily being in larger amount than the insoluble fibres. The lap of fibres should comprise at least 60% by weight, preferably at least 70% and better still at least 80% by weight of soluble fibres relative to the total weight of fibres. It may thus comprise, for example, more than 95% by weight, or even more than 99% by weight and even 100% by weight of water-soluble fibres relative to the total weight of fibres in the envelope or the laps.

When the lap of fibres contains insoluble fibres, the latter fibres may be made of any material usually used as insoluble fibres; they may be, for example, silk fibre, cotton fibre, wool fibre, flax fibre, polyamide (Nylon®) fibre, polylactic acid fibre, modified cellulose (rayon, viscose or rayon acetate) fibre, poly-p-phenyleneterephthalamide fibre, especially Kevlar® fibre, polyolefin fibre and especially polyethylene or polypropylene fibre, glass fibre, silica fibre, aramid fibre, carbon fibre, especially in graphite form, Teflon® fibre, insoluble collagen fibre, polyester fibre, polyvinyl or polyvinylidene chloride fibre, polyethylene terephthalate fibre, and fibres formed from a mixture of the compounds mentioned above, for instance polyamide/polyester or viscose/polyester fibres.

In addition, the envelope and the laps of the invention may be woven or nonwoven.

According to a particular embodiment, the envelope and the laps of the invention are woven. In the context of the present invention, a "woven" material results from an organized assembly of fibres, in particular of water-soluble polymeric fibres, and more particularly of an intercrossing, in the same plane, of the said fibres, arranged in the warp direction and of fibres arranged perpendicular to the warp fibres, in the weft direction. The binding obtained between these warp and weft fibres is defined by a weave.

Such a woven material results from an operation directed towards assembling the fibres in an organized manner such as weaving per se, but may also result from knitting.

More particularly, the two layers or laps comprising the woven polymeric water-soluble fibres that constitute the envelope of the packaging article used in the process of the invention do not comprise any other additional layer superposed thereon.

According to another particularly advantageous mode of the invention, the envelope and the laps are nonwoven.

Nonwovens are described in general in Riedel's "Nonwoven Bonding Methods & Materials", Nonwoven World (1987), which is incorporated herein by reference.

For the purposes of the present invention, the term "nonwoven" means a substrate comprising fibres, in particular water-soluble polymeric fibres, in which substrate the individual fibres are arranged in a disordered manner in a structure in the form of a lap and which are neither woven nor knitted. The fibres of the nonwoven are generally bonded together, either under the effect of a mechanical action (for example needle punching, air jet, water jet, etc.), or under the effect of a thermal action, or by addition of a binder.

Such a nonwoven is, for example, defined by standard ISO 9092 as a web or lap of directionally or randomly orientated fibres, bonded by friction and/or cohesion and/or adhesion, excluding paper and products obtained by weaving, knitting, tufting or stitching incorporating binding yarns or filaments.

A nonwoven differs from a paper by virtue of the length of the fibres used. In paper, the fibres are shorter. However, there are nonwovens based on cellulose fibre, which are manufactured by a wet-laid process and that have short fibres as in paper. The difference between a nonwoven and a paper is generally the absence of hydrogen bonding between the fibres in a nonwoven.

Very preferentially, the fibres used in the context of the present invention are chosen from synthetic fibres such as PVA fibres. In particular, the envelope and laps of the invention are nonwoven, and preferentially made of nonwoven PVA fibres.

To produce the water-soluble and preferably nonwoven lap(s) of the envelope of the packaging article, use is preferably made of PVA fibres that are soluble in water at a temperature of less than or equal to 35° C., for instance the fibres sold by the Japanese company Kuraray under the name Kuralon K-II, and particularly the grade WN2 which is soluble at and above 20° C. These fibres are described in document EP-A-636 716 which teaches the manufacture of PVA fibres that are soluble in water at temperatures not exceeding 100° C., by spinning and drawing the polyvinyl alcohol polymer in dry or wet form in the presence of solvents participating in the dissolution and solidification of the fibre. The fibre thus obtained may lead to the production of woven or nonwoven substrates. According to a particular mode of the invention, the PVA fibres of the examples of EP-A-636 716 are used, especially Example 2 and Comparative Example 1: commercial product Solvron SS.

These fibres may also be prepared from a solution to be spun, by dissolving a water-soluble PVA-based polymer in a first organic solvent, spinning the solution in a second organic solvent to obtain solidified filaments and wet-drawing of the filaments from which the first solvent is removed, and which are then dried and subjected to a heat treatment. The cross-section of these fibres may be substantially circular. These fibres have a tensile strength of at least 2.7 g/dtex (3 g/d). Patent application EP-A-0 636 716 describes such PVA-based water-soluble fibres and the process for manufacturing them. For example, the fibres may also be formed by extrusion and deposited on a conveyor to form a lap of fibres which is then consolidated via a standard fibre bonding technique, for instance needle-bonding, hot-bonding, calendering or air-through bonding, in which technique the water-soluble lap passes through a tunnel in which hot air is blown, or hydroentanglement directed towards bonding the fibres via the action of fine jets of water at very high pressure, which cannot be applied to fibres whose dissolution temperature is too low pressure.

As has been seen previously, the invention is not limited to the use of PVA, and use may also be made of fibres made of other water-soluble materials, provided that these materials dissolve in water having the desired temperature, for example the polysaccharide fibres sold under the name Lysorb by the company Lysac Technologies, Inc. or other fibres based on polysaccharide polymers such as glucomannans or starches.

The laps of the envelope may comprise a mixture of various fibres that are soluble in water at various temperatures (up to 35° C.).

The fibres may be composite, and they may comprise, for example, a core and a sheath not having the same nature, for example formed from different grades of PVA.

According to a particular embodiment of the invention, the lap(s) of the envelope are a nonwoven comprising water-soluble fibres, alone or as a mixture with insoluble fibres as indicated above, with not more than 40% by weight of insoluble fibres relative to the total weight of the fibres constituting the lap. Preferably, the nonwoven consists essentially of water-soluble fibres, i.e. it does not contain any insoluble fibres.

The envelope may have any shape that is suitable for the intended use, for example a rectangular, circular or oval shape, and it preferably has dimensions that enable it to be held between at least two fingers. Thus, the envelope or the laps may have, for example, an ovoid shape from about 2 to 10 cm long and from about 0.5 to 4 cm wide, or a circular disc shape from about 2 to 10 cm in diameter, or a square shape with a side length from about 5 to 15 cm, or a rectangular shape with a length from about 5 to 25 cm, it being understood that it may have any other shape and size that are suitable for the desired use.

Advantageously, the envelope and the laps have a low thickness, the laps possibly consisting of several layers. Preferably, the thickness of the envelope and of the laps ranges from 3% to 99.9% of its other dimensions. This thickness is especially less than 100 mm. The envelope and the laps are thus substantially flat, thin slices.

The surface delimiting the cavity(ies) has an area generally less than 625 $cm^2$, for example between 400 $cm^2$ and 0.025 $cm^2$.

Use may be made, for example, of an envelope and laps as defined in French patent application FR 12/61120 filed on 22 Nov. 2012 by the Applicant.

The article according to the present invention may comprise one or more water-soluble nonwoven laps and envelope.

Preferentially, the amount of the envelope present in the article according to the invention is inclusively between 0.5% and 20.0% by weight relative to the total weight of the said article, advantageously inclusively between 1.0% and 10.0%, particularly inclusively between 2.0% and 5.0% and more particularly 3% by weight relative to the total weight of the packaging article.

FIG. 1a) shows a cross section of a particular embodiment of the packaging article comprising the envelope i) consisting of two laps, which are preferably water-soluble, 11 and 12, joined together at a peripheral region 14. Preferably, the two laps are joined by any suitable fixing means such as glueing, welding, especially heat-welding, in particular by entanglement. The first lap 11 also has a free central region D arranged facing a free central region D of the second lap 12. These two central regions delimit a central cavity, the said cavity containing an anhydrous oxidizing composition 13 as defined previously comprising at least one anhydrous oxidizing agent optionally mixed with other powdered ingredients.

The laps 11 and 12 have a closed outer perimeter 15. The shape of the outer perimeter 15 is, for example, rounded, such as circular or elliptical, or polygonal, such as square, rectangular or triangular, preferably circular.

Figure 1B:
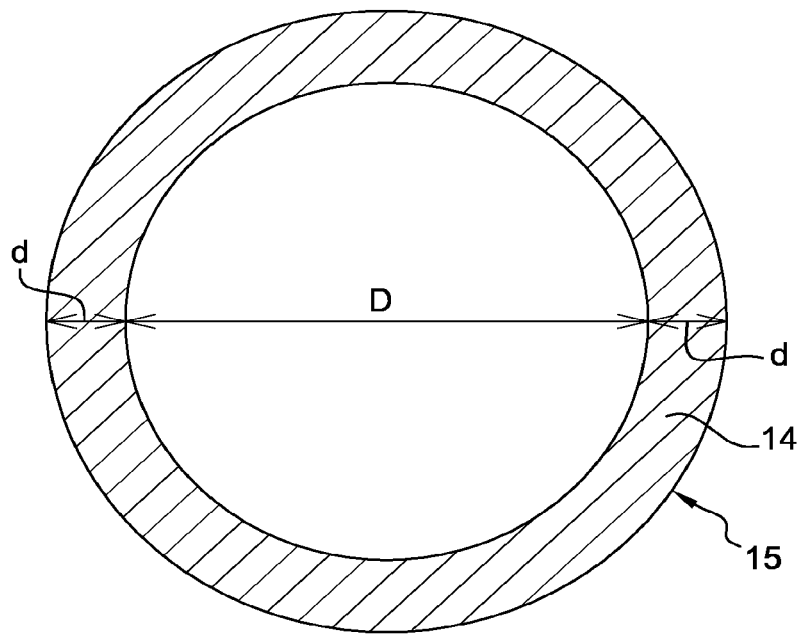

FIG. 1b) shows a top view of the packaging article as described in FIG. 1a), in which part D corresponds to the cavity or "central region" in which is found the anhydrous bleaching composition 13, and d corresponds to the peripheral region hermetically joining the two laps 11 and 12.

Figure 1C:
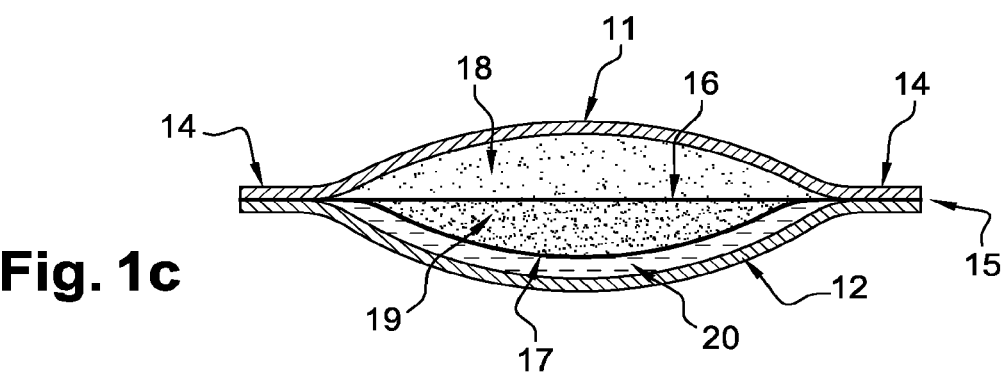
FIG. 1c shows a cross section of an exemplary embodiment of an alternate packaging article according to the disclosure.

FIG. 1c) shows a cross section of a particular embodiment of the packaging article, comprising an envelope consisting of two laps 11 and 12, which are preferably water-soluble, and comprising an additional lap 16, which is preferably water-soluble, and optionally other additional laps 17, which are preferably water-soluble, which define several cavities in which are housed the ingredients such as the anhydrous oxidizing composition as defined previously comprising at least one anhydrous oxidizing agent 18 as defined below, and optionally at least one alkaline agent 19 as defined below.

The first lap 11 has a thickness smaller than its other dimensions, for example less than 10% of its maximum transverse dimension D+2d.

The thickness of the first lap 11 is, for example, less than 10 mm and especially between 0.1 mm and 3 mm. Its maximum transverse dimension D+d is, for example, less than 100 mm, and is especially inclusively between 10 mm and 60 mm.

The first lap 11 thus forms a layer, for example made of nonwoven, which can itself consist of several layers of nonwovens that are consolidated together.

The second lap 12 also has a closed outer perimeter 15. The outer perimeter 15 of the first layer 11 substantially identical in shape to the outer perimeter 15 of the second layer 12.

The second lap 12, which is preferably water-soluble, has a thickness smaller than its other dimensions, for example less than 10% of its maximum transverse dimension D+2d.

The thickness of the second lap 12, which is preferably water-soluble, is, for example, less than 10 mm and especially between 0.1 mm and 3 mm. Its maximum transverse dimension D+2d is less than 100 mm, and is especially between 10 mm and 60 mm.

The thickness is advantageously measured according to the standard EDANA WSP 120.1(5).

The second lap 12 is advantageously a nonwoven.

The first lap 11 and the second lap 12, which may be identical or of different thicknesses, densities and/or composition, are preferably nonwovens that are water-soluble at a temperature of less than or equal to 35° C. The nonwoven laps and envelope are soluble in an aqueous solution, such as water. The nonwoven envelope and laps are preferentially made of PVA.

Figure 1D:
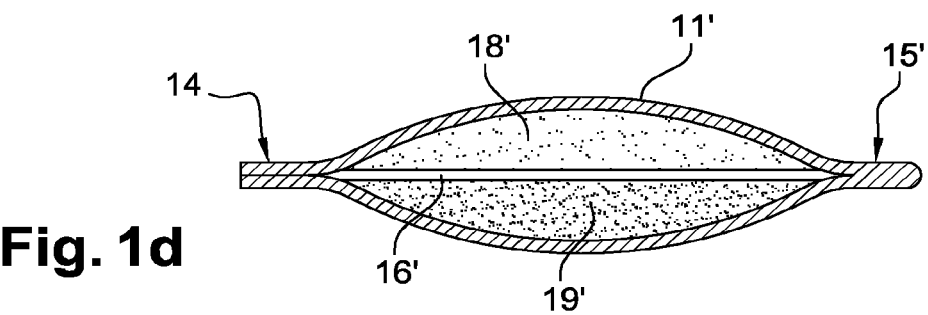
FIG. 1d shows a cross section of an alternate configuration for exemplary embodiment in FIG. 1c.
Figure 1E:
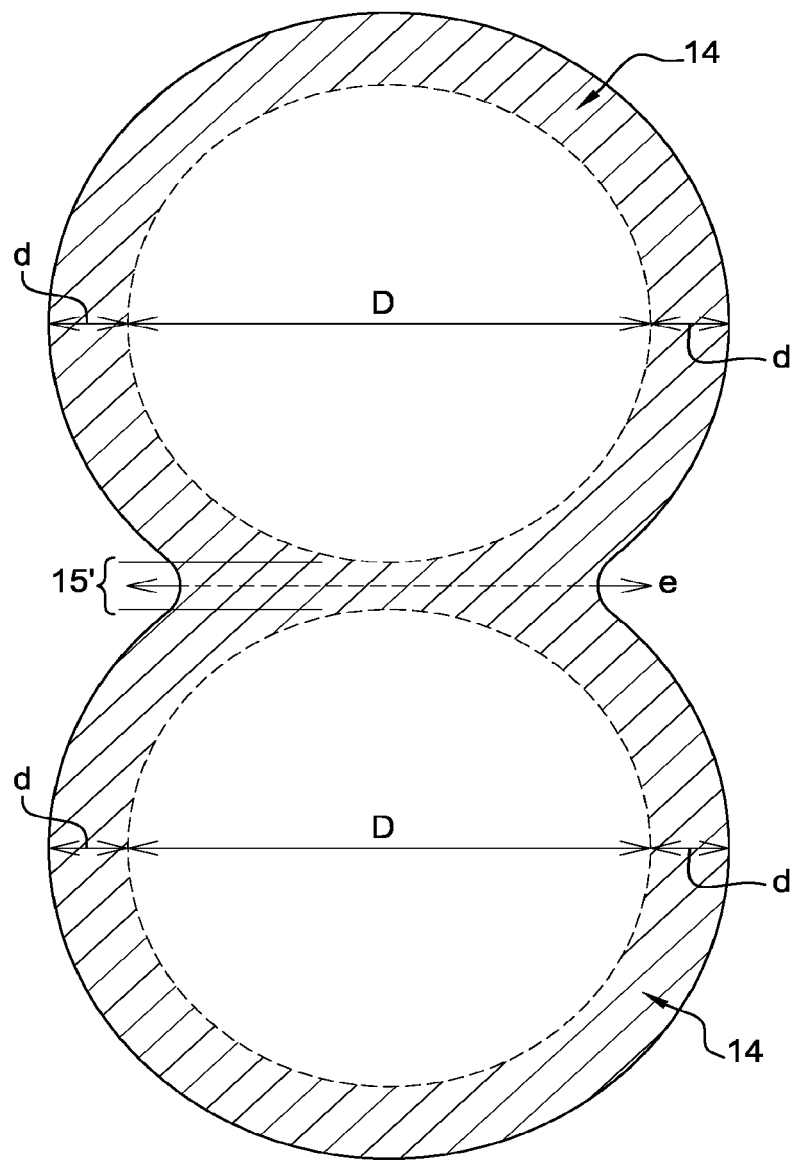
FIG. 1e shows a top view of the exemplary embodiment in FIG. 1d.

As a variant, the second lap may be formed by the first lap folded on itself 11' shown in FIG. 1d) in cross-section and FIG. 1e) in top view. The lap is folded on itself along the folding axis e which defines a cavity in which is found the oxidizing composition as defined previously and hereinbelow comprising at least one anhydrous chemical oxidizing agent 18' as defined below, and optionally at least one alkaline agent as defined below, preferably in powder form, and/or excipients as defined below, which are preferably in powder form 19', optionally separated by one or more water-soluble laps 16'. The lap 11', once filled with the ingredients 19' and with the water-soluble lap(s) 16', is folded along the axis e, forming a folding zone 15' and then joined at a peripheral region 14, the shaded part of figure e), preferably via any suitable fixing means such as glueing, welding, especially heat-welding, and in particular by entanglement. The thickness of the water-soluble lap 11' and the transverse dimensions satisfy the same criteria as those defined for the lap 11 or 12 of FIG. 1b).

The fibres forming the first lap 11 or 11' and the second lap 12, and the additional laps 16, 16' and 17, are preferably water-soluble, i.e. they consist of water-soluble fibres. These fibres are, for example, nonwoven water-soluble fibres such as PVA fibres, polysaccharide fibres such as glucomannans or starches, or any other polymer or compound that is capable of forming water-soluble fibres or yarns, obtained, for example, by extrusion.

The laps 11, 11' and 12 and the optional additional laps 16, 16' and 17, which are preferentially made of nonwoven, generally have a basis weight of less than or equal to 60 g/m$^2$, or even less than or equal to 50 g/m$^2$ and better still less than or equal to 45 g/m$^2$. In a variant, the basis weight of at least one layer may be greater than 60 g/m$^2$.

The packaging articles comprising water-soluble fibres used in the process according to the invention are preferably soluble in water or in an aqueous composition with a dissolution time of the packaging article preferably of not more than one hour.

Process for Preparing the Packaging Article:

The envelope i) delimits or defines a cavity that is filled with an anhydrous oxidizing composition ii) as defined previously, preferably in powder or paste form, comprising at least one anhydrous chemical oxidizing agent as defined below, and optionally at least one alkaline agent, preferably in powder or paste form, the article is then closed by folding the envelope i) as defined previously on itself with its contents, followed by assembly at its periphery, for example by glueing or welding, preferably by heat-welding, or alternatively, if the article contains an envelope consisting of two laps, an anhydrous oxidizing composition ii) preferably in powder or paste form, is placed on the first lap, the article is closed by means of a second lap which covers the ingredients ii) placed on the first lap and which is assembled, for example, by glueing or welding at its periphery, preferably by heat-welding at its periphery, so as to obtain a hermetic article, which does not allow the powders or pastes contained in the said article to pass into the atmosphere. When the envelope and the laps comprise several water-soluble laps of nonwovens, these nonwovens may be assembled especially by heat-welding at their periphery. Preferably, the heat-welding is performed with entanglement of the fibres of the parts of the envelope to be welded.

ii) Chemical Oxidizing Agent

As has been indicated previously, the anhydrous oxidizing composition comprises at least one anhydrous chemical oxidizing agent which may be in paste or powder form, preferably in powder form.

The expression "chemical oxidizing agent" means an oxidizing agent other than atmospheric oxygen.

The anhydrous chemical oxidizing agent may be chosen from peroxygenated salts, for instance persulfates, perborates, peracids and precursors thereof or percarbonates of alkali metals or alkaline-earth metals, such as sodium carbonate peroxide, also known as sodium percarbonate; alkali metal bromates or ferricyanides, solid hydrogen peroxide-generating chemical oxidizing agents such as urea peroxide and polymer complexes that can release hydrogen peroxide, especially those comprising a heterocyclic vinyl monomer such as polyvinylpyrrolidone/H$_2$O$_2$ complexes, in particular in powder form; oxidases that produce hydrogen peroxide in the presence of a suitable substrate (for example glucose in the case of glucose oxidase or uric acid with uricase), and mixtures thereof.

Preferably, the persulfate(s) are chosen from sodium, potassium and ammonium persulfates, and mixtures thereof.

As regards the complexes of hydrogen peroxide and of polymer containing as monomer at least one heterocyclic vinyl monomer, the heterocyclic vinyl monomer may be chosen from monomers comprising a 4- to 6-membered heterocycle, optionally fused to a benzene ring and comprising from 1 to 4 identical or different endocyclic heteroatoms; the number of endocyclic heteroatoms being less than the number of ring members of the heterocycle. Preferably, the number of endocyclic heteroatoms is 1 or 2.

More particularly, the heteroatom(s) are chosen from sulfur, oxygen and nitrogen, preferably from nitrogen and oxygen. In accordance with an even more advantageous embodiment of the invention, the monomer comprises at least one endocyclic nitrogen atom.

The vinyl heterocycle may optionally be substituted with one or more $C_1$-$C_4$ and preferably $C_1$-$C_2$ alkyl groups.

Preferably, the heterocyclic monomer is chosen from N-vinyl monomers.

Among the monomers that may be envisaged, mention may be made of the following optionally substituted monomers: N-vinylpyrrolidone, vinylcaprolactam, N-vinylpiperidone, N-vinyl-3-morpholine, N-vinyl-4-oxazolinone, 2-vinylpyridine, 4-vinylpyridine, 2-vinylquinoline, 1-vinylimidazole, 1-vinylcarbazole. Preferably, the monomer is optionally substituted N-vinylpyrrolidine.

According to a particularly advantageous embodiment of the invention, the polymer is a homopolymer.

However, it is not excluded to use a copolymer. In such a case, the comonomer(s) are chosen from vinyl acetate, (meth)acrylic acids, (meth)acrylamides and $C_1$-$C_4$ alkyl esters of (meth)acrylic acid, which may be substituted or unsubstituted.

The polymer participating in this complex may furthermore be water-soluble or water-insoluble. Preferably, it is water-soluble. It may have variable average molecular weights, preferably between $10^3$ and $3 \times 10^6$ g/mol and preferably between $10^3$ and $2 \times 10^6$ g/mol. It is also possible to use mixtures of such polymers.

Advantageously, the said complex comprises from 10% to 30% by weight, more particularly from 13% to 25% by weight and preferably from 18% to 22% by weight of hydrogen peroxide relative to the total weight of the complex.

According to an even more advantageous variant of the invention, in this complex, the mole ratio between the heterocyclic vinyl monomer(s) and the hydrogen peroxide ranges from 0.5 to 2 and preferably from 0.5 to 1.

This complex is advantageously in the form of a substantially anhydrous powder, i.e. a powder containing less than 5% by weight of water.

Complexes of this type are especially described in U.S. Pat. Nos. 5,008,106, 5,077,047, EP 832 846, EP 714 919, DE 4344131 and DE 195 45 380 and the other polymer complexes described in U.S. Pat. Nos. 5,008,093, 3,376,110 and 5,183,901.

Examples of complexes that may be mentioned include products such as Peroxydone K-30, Peroxydone K-90 and Peroxydone XL-10 and also complexes formed with hydrogen peroxide and one of the following polymers such as Plasdone K-17, Plasdone K-25, Plasdone K-29/32, Plasdone K-90, Polyplasdone INF-10, Polyplasdone XL-10, Polyplasdone XL, Plasdone S-630, Styleze 2000 Terpolymer, the series of Ganex copolymers, sold by the company ISP.

Preferably, the chemical oxidizing agent is chosen from peroxygenated salts, preferably from alkali metal or alkaline-earth metal persulfates or percarbonates such as sodium carbonate peroxide, also known as sodium percarbonate, polymer complexes that can release hydrogen peroxide, especially those comprising a heterocyclic vinyl monomer such as polyvinylpyrrolidone/$H_2O_2$ complexes, and mixtures thereof.

Preferably also, the chemical oxidizing agent is chosen from alkali metal or alkaline-earth metal percarbonates such as sodium percarbonate.

The concentration of anhydrous chemical oxidizing agents in the oxidizing composition in accordance with the invention generally ranges inclusively from 10% to 97% by weight, preferably from 30% to 90% by weight, better from 50% to 85% by weight and better still from 60% to 85% relative to the total weight of the oxidizing composition.

Other Ingredients

The packaging article used in the process according to the invention may contain other ingredients.

The packaging article may especially contain iii) one or more alkaline agents.

The alkaline agent(s) may be in the packaging article either combined with the anhydrous chemical oxidizing agents ii), or separated from the oxidizing agents by one or more laps as defined previously.

The alkaline agent(s) may be chosen, for example, from mineral alkaline agents such as dibasic or tribasic ammonium phosphate, water-soluble silicates such as alkali metal or alkaline-earth metal silicates, for instance sodium disilicate, sodium metasilicate, alkali metal or alkaline-earth metal phosphates or carbonates such as lithium, sodium, potassium, magnesium, calcium or barium phosphate or carbonate, and mixtures thereof, and organic alkaline agents such as alkanolamines.

Preferably, the alkaline agent(s) are mineral and are preferably chosen from water-soluble silicates such as alkali metal or alkaline-earth metal silicates, and alkali metal or alkaline-earth metal carbonates, and mixtures thereof.

In the context of the invention, the term "water-soluble silicate" means a silicate which has a solubility in water of greater than 0.5% preferably greater than 1% by weight at 25° C. These water-soluble silicates differ from aluminium silicates and derivatives thereof, especially clays, such as mixed silicates of natural or synthetic origin that are insoluble in water.

The concentration of alkaline agents is generally between 0.1% and 40% by weight, preferably between 0.5% and 30% by weight and better still between 1% and 25% by weight relative to the total weight of the oxidizing composition or of the packaging agent.

According to a particular embodiment of the invention, the packaging article contains iv) one or more ammonium salts.

The ammonium salt(s) that may be in the packaging article are either combined with the oxidizing agent(s), or separated from the oxidizing agents by one or more water-soluble or liposoluble laps as defined previously defining a cavity in which the said salt(s) are housed.

According to a particular variant, the packaging article comprises one or more ammonium salts chosen from ammonium halides such as ammonium chloride, ammonium sulfate, ammonium phosphate and ammonium nitrate.

In accordance with an even more advantageous embodiment of the invention, the ammonium salt is ammonium chloride or ammonium sulfate.

The concentration of ammonium salt(s), if they are present, is advantageously between 0.01% and 40% by weight relative to the total weight of the composition(s) contained in the packaging article, and preferably from 0.1% to 30% by weight relative to the total weight of the composition(s) contained in the packaging article.

When the oxidizing composition according to the invention is in paste form, it may also comprise v) one or more liquid fatty substances.

For the purposes of the present invention, the term "liquid fatty substance" means any fatty substance that is capable of flowing at room temperature, generally between 15° C. and 40° C., and at atmospheric pressure, under the action of its own weight.

Examples of liquid fatty substances that may be mentioned include the polydecenes of formula $C_{10n}H_{[(20n)+2]}$ in which n ranges from 3 to 9 and preferably from 3 to 7, esters and in particular esters of fatty alcohols or of fatty acids, sugar esters or diesters of $C_{12}$-$C_{24}$ fatty acids, cyclic esters, cyclic ethers, silicone oils, mineral oils, plant oils or animal oils, or mixtures thereof.

Preferably, the liquid fatty substance(s) are chosen from the polydecenes of formula $C_{10n}H_{[(20n)+2]}$ in which n ranges from 3 to 9 and preferably from 3 to 7, esters of fatty alcohols or of fatty acids, liquid petroleum jelly or liquid paraffin, and mixtures thereof.

Preferably, one or more mineral oils may be present in the packaging article, in particular combined with the anhydrous chemical oxidizing agent(s), for instance liquid paraffin or petroleum jelly, preferably petroleum jelly.

In the composition(s) contained in the packaging article, the content of liquid fatty substance(s), if they are present, advantageously ranges from 10% to 50% by weight relative to the weight of the composition(s) contained in the packaging article, and preferably from 20% to 50% by weight relative to the weight of the composition(s) contained in the packaging article.

The anhydrous composition according to the invention in paste form and comprising a liquid fatty substance may be advantageously prepared by dispersing, under mechanical action, all of the compounds that are in powder form in the liquid fatty substance, in which the other liquid compounds of the composition have been predispersed or premixed.

The paste may also be prepared by extrusion, by introducing the liquid and solid phases of the composition into an extruder and then mixing them at a temperature below 25° C. using a co-rotating twin-screw system composed of transportation and blending elements.

According to a particular embodiment, the packaging article of the invention comprises vi) one or more thickening polymers. These polymers may be present in the said article with the anhydrous chemical oxidizing agent(s), or separated from the other ingredients by one or more water-soluble laps as defined previously. Advantageously, the thickening polymers are chosen from the following polymers:

(a) nonionic amphiphilic polymers comprising at least one fatty chain and at least one hydrophilic unit;
(b) anionic amphiphilic polymers comprising at least one hydrophilic unit and at least one fatty-chain unit;
(c) crosslinked acrylic acid homopolymers;
(d) crosslinked homopolymers of 2-acrylamido-2-methylpropanesulfonic acid, and crosslinked acrylamide copolymers thereof which are partially or totally neutralized;
(e) ammonium acrylate homopolymers or copolymers of ammonium acrylate and of acrylamide;
(f) dimethylaminoethyl methacrylate homopolymers quaternized with methyl chloride or dimethylaminoethyl methacrylate copolymers quaternized with methyl chloride and acrylamide;

(g) polysaccharides such as:
(g1) scleroglucan gum (biopolysaccharide of microbial origin);
(g2) gums derived from plant exudates, such as gum arabic, ghatti gum, karaya gum or gum tragacanth; and
(g3) celluloses and derivatives;
(g4) guar gums and derivatives; or
(g5) starches or derivatives.

It should be noted that, in the case of the present invention, the thickening polymers act on the viscosity of the ready-to-use composition, i.e. the composition resulting from the mixing of the conditioning article according to the invention with an aqueous composition.

According to the invention, amphiphilic polymers are more particularly hydrophilic polymers that are capable, in the medium of the composition, and more particularly an aqueous medium, of reversibly combining with each other or with other molecules.

Their chemical structure more particularly comprises at least one hydrophilic region and at least one hydrophobic region. The term "hydrophobic group" means a radical or polymer bearing a saturated or unsaturated, linear or branched hydrocarbon-based chain, comprising at least 8 carbon atoms, preferably at least 10 carbon atoms, preferably from 10 to 30 carbon atoms, in particular from 12 to 30 carbon atoms and more preferentially from 18 to 30 carbon atoms. Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

The thickening polymers are preferably used in an amount that may range from 0.01% to 15% by weight relative to the weight of the composition(s) contained in the packaging article, and preferably from 0.1% to 10% by weight relative to the weight of the composition(s) contained in the packaging article.

According to a particular embodiment, the packaging article of the invention comprises vii) one or more surfactants. These surfactants may be present in the said article either with the oxidizing agent(s), or separated from the other ingredients by one or more water-soluble laps as defined previously, which define a cavity in which the surfactant(s) are housed. Preferably, vii) is found with the oxidizing agent(s) in the packaging article.

For the purposes of the present invention, the term "surfactant" means an agent comprising at least one hydrophilic group and at least one lipophilic group in its structure, and which is preferably capable of reducing the surface tension of water, and comprising in its structure, as optional repeating units, only alkylene oxide units and/or sugar units and/or siloxane units. Preferably, the lipophilic group is a fatty chain comprising from 8 to 30 carbon atoms.

This or these surfactants may be chosen from anionic, amphoteric, nonionic and cationic surfactants, or mixtures thereof.

More particularly, the surfactants are chosen from non-ionic and anionic surfactants. The surfactants that are suitable for performing the present invention are especially the following:

(a) Anionic surfactant(s):

The term "anionic surfactant" means a surfactant comprising, as ionic or ionizable groups, only anionic groups. These anionic groups are preferably chosen from the groups —C(O)OH, —C(O)O, —SO$_3$H, —S(O)$_2$O, —OS(O)$_2$OH, —OS(O)$_2$, —P(O)$_2$O$^-$, —P(O)O$_2^-$, —P(OH)$_2$, =P(O)OH, —P(OH)O$^-$, =P(O)$^-$, =POH and =PO$^-$, the anionic parts comprising a cationic counterion such as those derived from an alkali metal, an alkaline-earth metal, an amine or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids, and the corresponding non-salified forms of all these compounds, the alkyl and acyl groups of all these compounds comprising from 6 to 24 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts, and in particular the sodium or magnesium salts.

Among the anionic surfactants mentioned, use is preferably made of ($C_6$-$C_{24}$)alkyl sulfates, ($C_6$-$C_{24}$)alkyl ether sulfates comprising from 2 to 50 ethylene oxide units, especially in the form of alkali metal, ammonium, amino alcohol and alkaline-earth metal salts, or a mixture of these compounds.

In particular, it is preferred to use ($C_{12}$-$C_{20}$)alkyl sulfates and ($C_{12}$-$C_{20}$)alkyl ether sulfates comprising from 2 to 20 ethylene oxide units, especially in the form of alkali metal salts, ammonium salts, amino alcohol salts and alkaline-earth metal salts, or a mixture of these compounds. Better still, it is preferred to use sodium lauryl ether sulfate, in particular those containing 2.2 mol of ethylene oxide, more preferentially (C12-C20)alkyl sulfates such as an alkali metal lauryl sulfate such as sodium lauryl sulfate.

(b) Amphoteric surfactant(s):

The amphoteric or zwitterionic surfactant(s) of the invention are preferably non-silicone, and are especially derivatives of optionally quaternized aliphatic secondary or tertiary amines, in which derivatives the aliphatic group is a linear or branched chain comprising from 8 to 22 carbon atoms, the said amine derivatives containing at least one anionic group, for instance a carbon/late, sulfonate, sulfate, phosphate or phosphonate group. Mention may be made in particular of ($C_8$-$C_{20}$)alkylbetaines, sulfobetaines, ($C_8$-$C_{20}$) alkylamido($C_3$-$C_8$)alkylbetaines and ($C_8$-$C_{20}$)alkylamido ($C_6$-$C_8$)alkylsulfobetaines.

Among the amphoteric or zwitterionic surfactants mentioned above, use is preferably made of $(C_8-C_{20})$alkylbetaines such as cocoylbetaine, and $(C_8-C_{20})$alkylamido$(C_3-C_8)$alkylbetaines such as cocamidopropylbetaine, and mixtures thereof. More preferentially, the amphoteric or zwitterionic surfactant(s) are chosen from cocamidopropyl betaine and cocoylbetaine.

(c) Cationic surfactant(s):

The cationic surfactant(s) that may be used in the composition according to the invention comprise, for example, optionally polyoxyalkylenated primary, secondary or tertiary fatty amine salts, quaternary ammonium salts, and mixtures thereof.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride and dipalmitoylethylhydroxyethylammonium methosulfate, and mixtures thereof.

(d) Nonionic surfactant(s):

Examples of nonionic surfactants that may be used in the composition used according to the invention are described, for example, in "Handbook of Surfactants" by M. R. Porter, published by Blackie & Son (Glasgow and London), 1991, pp. 116-178.

Examples of nonionic surfactants that may be mentioned include:
oxyalkylenated $(C_8-C_{24})$alkylphenols;
saturated or unsaturated, linear or branched, oxyalkylenated or glycerolated $C_8-C_{30}$ alcohols;
saturated or unsaturated, linear or branched, oxyalkylenated $C_8-C_{30}$ amides;
esters of saturated or unsaturated, linear or branched, $C_8-C_{30}$ acids and of polyethylene glycols;
polyoxyethylenated esters of saturated or unsaturated, linear or branched, $C_8-C_{30}$ acids and of sorbitol;
fatty acid esters of sucrose;
$(C_8-C_{30})$alkylpolyglycosides, $(C_8-C_{30})$alkenylpolyglycosides, optionally oxyalkylenated (0 to 10 oxyalkylene units) and comprising 1 to 15 glucose units, $(C_8-C_{30})$ alkylglucoside esters;
saturated or unsaturated, oxyethylenated plant oils;
condensates of ethylene oxide and/or of propylene oxide, inter alia, alone or as mixtures;
N—$(C_8-C_{30})$alkylglucamine and N—$(C_8-C_{30})$acylmethylglucamine derivatives;
aldobionamides;
amine oxides;
oxyethylenated and/or oxypropylenated silicones;
the surfactants containing a number of moles of ethylene oxide and/or of propylene oxide ranging advantageously from 1 to 100, more particularly from 2 to 100, preferably from 2 to 50 and more advantageously from 2 to 30. Advantageously, the nonionic surfactants do not comprise any oxypropylene units.

In accordance with a preferred embodiment of the invention, the nonionic surfactants are chosen from oxyethylenated $C_8-C_{30}$ alcohols comprising from 1 to 100 mol and more particularly from 2 to 100 mol of ethylene oxide; polyoxyethylenated esters of saturated or unsaturated, linear or branched $C_8-C_{30}$ acids and of sorbitan comprising from 1 to 100 mol and better still from 2 to 100 mol of ethylene oxide.

As examples of monoglycerolated or polyglycerolated nonionic surfactants, monoglycerolated or polyglycerolated $C_8-C_{40}$ alcohols are preferably used.

In particular, the monoglycerolated or polyglycerolated $C_8-C_{40}$ alcohols preferably correspond to formula (A8) below:

$$R_{29}O—[CH_2—CH(CH_2OH)—O]_m—H \quad (A8)$$

in which formula (A8):
$R_{29}$ represents a linear or branched $C_8-C_{40}$ and preferably $C_8-C_{30}$ alkyl or alkenyl radical; and
m represents a number ranging from 1 to 30 and preferably from 1 to 10.

As examples of compounds of formula (A8) that are suitable within the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (A8) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

Preferentially, the nonionic surfactant used in the process of the invention in the composition is a monooxyalkylenated or polyoxyalkylenated, particularly monooxyethylenated or polyoxyethylenated, or monooxypropylenated or polyoxypropylenated, nonionic surfactant, or a combination thereof, more particularly monooxyethylenated or polyoxyethylenated, monoglycerolated or polyglycerolated surfactants and alkylpolyglucosides.

Even more preferentially, the nonionic surfactants are chosen from polyoxyethylenated sorbitan esters, polyoxyethylenated fatty alcohols and alkylpolyglucosides, and mixtures thereof.

The surfactant(s) when they are present, more particularly represent between 0.01% and 60% by weight relative to the total weight of the composition(s) included in the packaging article, preferably between 0.5% and 30% by weight and even more preferentially between 1% and 20% by weight of the composition(s) included in the packaging article.

According to a particular embodiment, the packaging article of the invention comprises viii) one or more cationic or amphoteric substantive polymers. These polymers may be found in the said article either with the anhydrous chemical oxidizing agent(s), or separated from the other ingredients by one or more water-soluble laps as defined previously, which define a cavity in which the substantive polymer(s) are housed. Preferably, ix) is found with the oxidizing agent(s) in the packaging article. More particularly, the substantive polymers are chosen from cationic polymers.

The substantive character (i.e. the capacity for deposition on the hair) of the polymers is determined conventionally using the test described by Richard J. Crawford, Journal of the Society of Cosmetic Chemists, 1980, 31-(5)-pages 273 to 278 (detection by Red 80 acid dye).

These substantive polymers are especially described in the literature in patent application EP-A-0 557 203.

Among the substantive polymers of the dimethyldiallylammonium halide homopolymer or copolymer type that may be used according to the invention, mention may be made in particular of:

diallyldimethylammonium chloride polymers such as Polyquaternium-6;

the copolymers of diallyldimethylammonium chloride and of acrylic acid such as that with proportions (80/20 by weight) sold under the name Merquat 280 Dry by the company Calgon;

copolymers of dimethyldiallylammonium chloride and of acrylamide.

Among the substantive polymers of the methacryloyloxyethyltrimethylammonium halide polymer type that may be used according to the invention, mention may be made in particular of the products that are known in the CTFA dictionary (5th edition, 1993) as Polyquaternium 37, Polyquaternium 32 and Polyquaternium 35, which correspond respectively, as regards Polyquaternium 37, to crosslinked poly(methacryloyloxyethyltrimethylammonium chloride), in dispersion at 50% in mineral oil, and sold under the name Salcare SC95 by the company Allied Colloids, as regards Polyquaternium 32, to the crosslinked copolymer of acrylamide and methacryloyloxyethyltrimethylammonium chloride (20/80 by weight), in dispersion at 50% in mineral oil, and sold under the name Salcare SC92 by the company Allied Colloids, and as regards Polyquaternium 35, to the methosulfate of the methacryloyloxyethyltrimethylammonium/methacryloyloxyethyldimethylacetylammonium copolymer.

The substantive polymers of the quaternary polyammonium type that can be used according to the invention are as follows:

polymers consisting of repeating units corresponding to formula ($\alpha$) below:

—$(CH_3)_2N^+$—$(CH_2)_3$—$(CH_3)_2N^+$—$(CH_2)_6$—, $2X^-$ with $X^-$, which may be identical or different, representing an anionic counterion as defined previously, in particular a halide such as $Cl^-$, these polymers being prepared and described in French patent 2 270 846; preference is given to the polymers with repeating units of formula ($\alpha$) whose molecular weight, determined by gel permeation chromatography, is between 9500 and 9900;

polymers consisting of repeating units corresponding to formula ($\beta$) below:

—$(CH_3)_2N^+$—$(CH_2)_3$—$(CH_3)_2N^+$—$(CH_2)_3$—, $2X^-$ with $X^-$ as defined for ($\alpha$), these polymers being prepared and described in French patent 2 270 846; preference is given to the polymers with repeating units of formula ($\beta$) whose molecular weight, determined by gel permeation chromatography, is about 1200;

polymers consisting of repeating units corresponding to formula ($\gamma$) below:

—$(CH_3)_2N^+$—$(CH_2)_p$—N(H)—C(O)-G-N(H)—$(CH_2)_p$—$(CH_3)_2N^+$—$(CH_2)_2$—O—$(CH_2)_2$—, $2X^-$ in which p denotes an integer ranging from 1 to 6 approximately, G may represent a bond or a group —$(CH_2)_r$—C(O)— in which r denotes an integer equal to 4 or 7, these polymers being prepared and described in patents U.S. Pat. Nos. 4,157,388, 4,390,689, 4,702,906 and 4,719,282; preference is given to the polymers with repeating units of formula ($\gamma$) whose molecular weight is less than 100 000 and preferably less than or equal to 50 000.

The packaging article used in the process of the invention may also comprise other additives conventionally used in cosmetics.

The packaging article may thus in particular comprise fillers such as clays; hydrophilic or hydrophobic silicas; binders such as vinylpyrrolidone; lubricants such as polyol stearates or alkali metal or alkaline-earth metal stearates; pigments; direct dyes; matt-effect agents or opacifiers such as titanium oxides; antioxidants such as erythorbic acid; reducing agents such as sodium metabisulfite; penetrants or sequestrants such as tetraacetic ethylenediaminetetraacetic acid or salts thereof; moisture absorbers such as amorphous silicas, certain polyacrylates that are crosslinked or modified with hydrophobic groups, for instance the products Luquasorb 1010 from BASF, Polytrap 6603 Adsorber from Amcol; buffers; dispersants; film-forming agents; preserving agents; vitamins; fragrances; ceramides; conditioning agents other than the substantive polymers ix) and the cationic surfactants mentioned above.

The composition in accordance with the invention may also comprise agents for controlling the release of oxygen, such as magnesium carbonate or magnesium oxide.

The additives and the oxygen-release control agents as defined previously may be present in an amount, for each of them, of between 0.01% and 40% by weight and preferably between 0.1% and 30% by weight relative to the total weight of the composition or of the article.

Process for Treating Keratin Fibres

According to an embodiment, the process for treating keratin fibres is in particular a process for dyeing an/or bleaching keratin fibres such as the hair, comprising at least the following steps:

i) mixing the packaging article as defined previously with a composition that is capable of dissolving the envelope of the packaging article, ii) applying the resulting composition to the keratin fibres, iii) leaving the composition to stand on the fibres, iv) rinsing the said fibres, v) optionally shampooing the fibres, rinsing them and drying them.

It is clearly understood that, depending on the nature of the envelope, the composition that is capable of dissolving the envelope will be water or an aqueous composition when the envelope predominantly or solely contains a hydrophilic envelope, and the composition that is capable of dissolving the envelope will be an organic composition comprising an anhydrous or aqueous liquid fatty substance, when the article predominantly or solely contains lipophilic laps and envelopes.

Thus, the aqueous composition may simply be water. The aqueous composition may optionally comprise at least one organic polar solvent. Among the organic polar solvents that may be used in this composition, mention may be made of organic compounds that are liquid at room temperature (25° C.) and at least partially water-miscible. Examples that may be mentioned more particularly include alkanols such as ethyl alcohol, isopropyl alcohol, aromatic alcohols such as benzyl alcohol and phenylethyl alcohol, or polyols or polyol ethers, for instance ethylene glycol monomethyl, monoethyl or monobutyl ether, propylene glycol or ethers thereof, for instance propylene glycol monomethyl ether, butylene glycol, dipropylene glycol, and also diethylene glycol alkyl ethers, for instance diethylene glycol monoethyl ether or monobutyl ether.

More particularly, if one or more solvents are present, their respective content in the aqueous composition ranges from 0.5% to 20% and preferably from 2% to 10% by weight relative to the weight of the said aqueous composition.

According to one embodiment, the process as defined previously uses in the first step an aqueous composition which optionally comprises at least one basifying agent iii) as defined previously or optionally at least one ingredient chosen from: ammonium salts iv), preferably chosen from ammonium halides such as ammonium chloride, ammonium sulfate, ammonium phosphate and ammonium nitrate; liquid fatty substances v) preferably chosen from mineral oils, in particular liquid petroleum jelly; thickening polymers vi); surfactants viii), preferably nonionic or anionic surfactants, chosen in particular from $(C_{12}-C_{20})$alkyl sulfates and $(C_{12}-C_{20})$alkyl ether sulfates comprising from 2 to 20 ethylene oxide units, especially in the form of alkali metal salts, ammonium salts, amino alcohol salts and alkaline-earth metal salts, or a mixture of these compounds; preferably $(C_{12}-C_{20})$alkyl sulfates such as an alkali metal lauryl sulfate such as sodium lauryl sulfate; and cationic or amphoteric substantive polymers ix) as defined previously. These optional additives may be present in the packaging article. According to another particular variant of the invention, the composition that is capable of dissolving the envelope is an aqueous composition comprising a chemical oxidizing agent, preferably hydrogen peroxide, and optionally at least one basifying agent iii) or at least one ingredient as defined in the preceding variant, these alkaline agents and these ingredients possibly being present in the packaging article.

The weight concentration of hydrogen peroxide may be from 2% to 12% and preferably from 2% to 6% by weight of the aqueous composition.

Preferentially, the process as defined previously is such that the dilution ratio of one or more packaging articles as defined previously/the composition capable of dissolving the article(s), expressed on a weight basis, is inclusively between 10/90 and 90/10 and preferably between 10/90 and 50/50. Preferentially, this ratio is 20/80.

When the composition that is capable of dissolving the article is an aqueous composition comprising hydrogen peroxide, it preferably has a pH of less than 7. The acidic pH ensures the stability of the hydrogen peroxide in the composition. It may be obtained using acidifying agents, for instance hydrochloric acid, acetic acid, etidronic acid, phosphoric acid, lactic acid or boric acid, and it may be conventionally adjusted by adding basifying agents as defined above, all these compounds, needless to say, possibly being taken alone or as a mixture.

The pH of the resulting mixture is usually inclusively between 7 and 12. Preferably, the pH of the said mixture is usually inclusively between 7.5 and 11.

Once the mixing has been performed to obtain the ready-to-use composition, this composition is applied to the wet or dry human keratin fibres.

The leave-on time is generally between 1 minute and 1 hour and preferably from 10 minutes to 30 minutes.

The working temperature during the process is conventionally between room temperature (between 15 and 25° C.) and 80° C. and preferably between room temperature and 60° C.

After the treatment, the human keratin fibres are optionally rinsed with water, washed with shampoo, rinsed again with water, and then dried or left to dry.

The examples that follow illustrate the invention without, however, limiting its scope.

EXAMPLES

Example 1

I) The following compositions were prepared. The values are expressed as grams of active material for a composition total of 100 grams.

Composition A

| Sorbitol | 17 |
| Ammonium sulfate | 5 |
| Sodium carbonate peroxide or sodium percarbonate | 50 |
| Sodium metasilicate | 7.5 |
| Liquid petroleum jelly | 4 |
| Carboxymethylcellulose sodium salt | 5 |
| Hydroxyethylcellulose | 7.5 |
| Sodium lauryl sulfate | 1 |
| Nonwoven of polyvinyl alcohol (PVA) fibres with a mean diameter of about 10 microns | 3 |

II) Protocol for preparing the compositions and the packaging article

The packaging article is prepared in two stages: in a first stage, the ingredients are selected. The mixture of the powdered ingredients is then homogenized. In a second stage, the envelope is prepared from PVA which is in the form of two nonwoven laps joined together at the periphery, but leaving a part gaping allowing the introduction of ingredients. This double lap is in the form of a disc (5 cm in diameter and 3 mm thick).

The mixture of the said powdered ingredients is then introduced between the two PVA laps of the disc, and the gaping part is then closed.

An article comprising composition A in single-dose form containing 21.6 g is prepared according to the method indicated above.

At the time of use, the article is mixed with 78.4 g of tap water.

The mixture is applied to pigmented natural hair with a leave-on time of between 5 minutes and 1 hour and preferably between 10 minutes and 40 minutes.

The hair is rinsed and is then optionally shampooed, shampooing preferably being performed, and the hair is then dried.

Example 2

|  | Composition | |
| --- | --- | --- |
|  | B1 | B2 |
| Potassium persulfate | 27.42 | 27.42 |
| Hydroxypropylcellulose | 0.91 | 0.91 |
| PVP/H$_2$O$_2$ complex (Peroxydone XL-10 from Ashland) | 32.49 |  |
| Sodium carbonate peroxide or sodium percarbonate |  | 32.49 |
| Ammonium chloride | 2.91 | 2.91 |
| Sodium metasilicate | 9.32 | 9.32 |
| Nonwoven of polyvinyl alcohol (PVA) fibres with a mean diameter of about 10 microns | 26.95 | 26.95 |

Compositions B1 and B2 are prepared in the following manner:

In a first stage, the powdered ingredients, including the peroxygenated salts, the alkaline agents and the other chemical oxidizing agents, are selected. The mixture of the powdered ingredients is then homogenized. The PVA fibres (26.95 g per 73.05 g of pulverulent bleaching composition) are in the form of two nonwoven laps joined together at the periphery, but leaving a part gaping allowing the introduction of ingredients. This double lap is in the form of a disc (5 cm in diameter and 3 mm thick).

The mixture of the said powdered ingredients excluding the PVA is then introduced between the two PVA laps of the disc, and the gaping part is then closed.

Articles comprising each composition B1 and B2 in single-dose form containing 21.6 g are prepared according to the method indicated above.

At the time of use, each article is mixed with 78.4 g of water.

The mixture is applied to pigmented natural hair with a leave-on time of between 5 minutes and 1 hour and preferably between 10 minutes and 40 minutes.

The hair is rinsed and is then optionally shampooed, shampooing preferably being performed, and the hair is then dried.

The locks of pigmented hair are lightened by 1 to 2.5 tones depending on the starting hair (2.5 tones for natural chestnut-brown hair).

Furthermore, the application and localization of the compositions is easy and very pleasant, and the composition does not go outside the areas to be treated. It should be noted that the process is very easy to perform since it is a matter of dissolving the packaging article. Good bleaching of the hair is thus obtained, with great ease of use.

Example 3

The following composition according to the invention was prepared. The values are expressed as grams of active material for a composition total of 100 grams.

Composition C

|  | C |
| --- | --- |
| PPG-1-PEG-9 LAURYL GLYCOL ETHER | 4.4 |
| ULTRAMARINES | 0.5 |
| AMMONIUM CHLORIDE | 4.5 |
| CALCIUM STEARATE | 2 |
| MAGNESIUM CARBONATE | 2 |
| POTASSIUM CARBONATE | 2.3 |
| EDTA | 0.8 |
| SODIUM METASILICATE | 13.6 |
| SODIUM LAURYL SULFATE | 2 |
| SILICA | 4.2 |
| POTASSIUM PERSULFATE | 47 |
| SODIUM PERSULFATE | 10.9 |
| GUAR GUM | 1.8 |
| POLOXAMER 182 | 1 |
| CELLULOSE SHEET Dissolvo WLD60 | 3 |

In a first stage, the powdered ingredients, including the peroxygenated salts, the alkaline agents and the other chemical oxidizing agents, are selected. The mixture of the powdered ingredients is then homogenized. The cellulose sheet (3 g per 97 g of pulverulent bleaching composition) are in the form of two nonwoven laps joined together at the periphery, but leaving a part gaping allowing the introduction of ingredients. This double lap is in the form of a disc (5 cm in diameter and 3 mm thick).

The mixture of the said powdered ingredients is then introduced between the two cellulose laps of the disc, and the gaping part is then closed.

An article comprising composition C in single-dose form is prepared according to the method indicated above.

At the time of use, the article can be mixed with the following oxidizing composition D.

Composition D

| HYDROGEN PEROXIDE | 3.9 ma |
| --- | --- |
| PHOSPHORIC ACID | qs PH 2.2 |
| TETRASODIUM ETIDRONATE | 0.06 ma |
| TETRASODIUM PYROPHOSPHATE | 0.04 |
| SODIUM SALICYLATE | 0.035 |
| WATER | Qs 100 |

Example 4

The following compositions were prepared. The values are expressed as grams of active material for a composition total of 100 grams.

|  | Composition | |
| --- | --- | --- |
|  | E1 (comparative) | E2 (invention) |
| UREA | 3.88 | 3.88 |
| SODIUM PERSULFATE | 7.76 | 7.76 |
| AMMONIUM CHLORIDE | 4.365 | 4.365 |
| POTASSIUM PERSULFATE | 45.59 | 45.59 |
| EDTA | 0.97 | 0.97 |
| SODIUM METASILICATE | 11.64 | 11.64 |
| MAGNESIUM OXIDE | 0.97 | 0.97 |
| KAOLIN | 4.85 | 4.85 |
| TITANIUM DIOXIDE | 1.94 | 1.94 |
| VP/VA COPOLYMER (PVP/VA S 630 L ISP) | 1.746 | 1.746 |
| GUAR GUM | 2.619 | 2.619 |
| HYDROGENATED POLYDECENE | 1.649 | 1.649 |
| CETYL HYDROXYETHYLCELLULOSE | 0.97 | 0.97 |
| STEARETH-100/PEG-136/HDI COPOLYMER (RHEOLUXE 811 from ELEMENTIS) | 2.91 | 2.91 |
| POLYVINYL ALCOHOL FILM (Solublon PVAL-Film Type GA 40 μm) | 3 | — |
| Nonwoven of polyvinyl alcohol (PVA) fibres with a mean diameter of about 10 microns | — | 3 |
| SODIUM CETEARYL SULFATE | 0.97 | 0.97 |
| SODIUM LAURYL SULFATE | 2.231 | 2.231 |
| MAGNESIUM STEARATE | 1.94 | 1.94 |

At the time of use, each composition E1 and E2 is mixed with the oxidizing composition D (as described in example 3): 33 parts of E1 or E2 for 67 parts of D, composition D is first poured in a bowl and formulas E1 or E2 are introduced. After 15 seconds, the compounds are mixed until solubilisation of all the ingredients to obtain an homogeneous mixture.

Each mixture is applied to locks of natural chesnut hair (TH4) (10 g of mixture for 1 g of hair).

The mixture is left at 27° C. for 30 minutes. The hair is then rinsed, optionally washed with a standard shampoo and dried.

The colorimetric measurements were carried out using a Minolta 3600D spectrocolorimeter (illuminant D65, angle 10°, specular component included) in the CIELab system.

According to this system, L indicates the lightness. The lowest is the value of L, the most intense is the color of the hair.

ΔE represents the difference of color between the locks before and after application of the bleaching composition. The highest is the value of ΔE, the most important is the lightening.

The following results are obtained

|  | L* | a* | b* | ΔE |
| --- | --- | --- | --- | --- |
| Non treated locks | 20.35 | 2.47 | 2.87 | — |
| Locks treated with E1 + B | 28.67 | 8.89 | 13.85 | 15.20 |

-continued

|  | L* | a* | b* | ΔE |
|---|---|---|---|---|
| Locks treated with E2 + B (invention) | 31.94 | 9.45 | 17.39 | 19.85 |

The mixture E2 + B according to the invention allows to obtain higher L* and ΔE values, i.e. a better lightening of the fiber, than the mixture E1 + B (comparative).

The invention claimed is:

1. A process for treating keratin fibers, the process comprising:
   (i) mixing a packaging article with an aqueous composition comprising hydrogen peroxide to form a mixture having a pH ranging from 7 to 12,
      wherein the packaging article comprises polyvinyl alcohol fibers and defines at least one cavity, and
      wherein the at least one cavity comprises a substantially anhydrous composition comprising:
         at least one chemical oxidizing agent chosen from sodium persulfates, potassium persulfates, ammonium persulfates, or mixtures of two or more thereof, wherein the total amount of chemical oxidizing agents ranges from 30% to 90% by weight, relative to the weight of the substantially anhydrous composition,
         at least one alkaline agent chosen from alkali metal silicates, alkaline-earth metal silicates, alkali metal phosphates, alkaline-earth metal phosphates, alkali metal carbonates, alkaline-earth metal carbonates, or mixtures of two or more thereof, wherein the total amount of alkaline agents ranges from 1% to 25% by weight, relative to the weight of the substantially anhydrous composition,
         at least one anionic surfactant,
         at least one liquid fatty substance,
         at least one compound chosen from polyol stearates, alkali metal stearates, alkaline-earth metal stearates, or mixtures of two or more thereof, and
         at least one thickening polymer;
   (ii) applying the mixture to the keratin fibers;
   (iii) leaving the mixture on the keratin fibers for a leave-on time ranging from 1 minute to 1 hour; and
   (iv) rinsing the keratin fibers.

2. The process of claim 1, wherein the aqueous composition comprising hydrogen peroxide has a pH of less than 7.

3. The process of claim 2, wherein the hydrogen peroxide is present in an amount ranging from 2% to 12% by weight, relative to the total weight of the aqueous composition.

4. The process of claim 1, wherein the at least one chemical oxidizing agent is chosen from potassium persulfate, ammonium persulfate, or a mixture thereof.

5. The process of claim 1, wherein the at least one alkali agent is chosen from magnesium carbonate, sodium silicate, sodium metasilicate, or mixtures of two or more thereof.

6. The process of claim 1, wherein the substantially anhydrous composition is a powder.

7. The process of claim 1, wherein the at least one anionic surfactant is chosen from alkali metal salts, ammonium salts, amino alcohol salts or alkaline-earth metal salts of (C12-C20)alkyl sulfates or of (C12-C20)alkyl ether sulfates comprising from 2 to 20 ethylene oxide units, or mixtures of two or more thereof.

8. The process of claim 7, wherein the at least one anionic surfactant is chosen from sodium lauryl ether sulfate, sodium lauryl sulfate, or a mixture thereof.

9. The process of claim 1, wherein the at least one liquid fatty substance is chosen from esters of fatty alcohols, esters of fatty acids, sugar esters or diesters of C12-C24 fatty acids, cyclic esters, cyclic ethers, silicone oils, mineral oils, plant oils, animal oils, or mixtures of two or more thereof.

10. The process of claim 1, wherein the substantially anhydrous composition comprises sodium stearate.

11. The process of claim 1, wherein the at least one thickening polymer is chosen from scleroglucan gum, gums derived from plant exudates, celluloses, cellulose derivatives, guar gums, guar gum derivatives, starches, starch derivatives, or mixtures of two or more thereof.

12. The process of claim 1, wherein the substantially anhydrous composition comprises less than 0.5% water by weight, relative to the total weight of the substantially anhydrous composition.

13. The process of claim 1, wherein the weight ratio of the packaging article to the aqueous composition ranges from 10/90 to 50/50.

14. The process of claim 1, wherein the leave-on time ranges from 10 minutes to 40 minutes.

15. A process for treating keratin fibers, the process comprising:
   (i) mixing a packaging article with an aqueous composition comprising hydrogen peroxide to form a mixture having a pH ranging from 7 to 12,
      wherein the packaging article comprises polyvinyl alcohol fibers and defines at least one cavity, and
      wherein the at least one cavity comprises a substantially anhydrous composition comprising:
         at least one chemical oxidizing agent chosen from sodium persulfates, potassium persulfates, ammonium persulfates, or mixtures of two or more thereof, wherein the total amount of chemical oxidizing agents ranges from 30% to 90% by weight, relative to the weight of the substantially anhydrous composition,
         at least one alkaline agent chosen from magnesium carbonate, sodium silicate, sodium metasilicate, or mixtures of two or more thereof, wherein the total amount of alkaline agents ranges from 1% to 25% by weight, relative to the weight of the substantially anhydrous composition,
         at least one anionic surfactant chosen from sodium lauryl ether sulfate, sodium lauryl sulfate, or a mixture thereof,
         mineral oil,
         sodium stearate, and
         at least one thickening polymer chosen from guar gum,
         wherein the composition comprises less than 0.5% water by weight, relative to the substantially anhydrous composition;
   (ii) applying the mixture to the keratin fibers;
   (iii) leaving the mixture on the keratin fibers for a leave-on time ranging from 1 minute to 1 hour; and
   (iv) rinsing the keratin fibers.

16. The process of claim 15, wherein the leave-on time ranges from 10 minutes to 40 minutes.

17. The process of claim 15, wherein the aqueous composition comprising hydrogen peroxide has a pH of less than 7.

18. The process of claim 15, wherein the hydrogen peroxide is present in an amount ranging from 2% to 12% by weight, relative to the total weight of the aqueous composition.

19. The process of claim 15, wherein the weight ratio of the packaging article to the aqueous composition ranges from 10/90 to 50/50.

\* \* \* \* \*